(12) United States Patent
Mussmann et al.

(10) Patent No.: US 7,968,535 B2
(45) Date of Patent: Jun. 28, 2011

(54) USE OF AZAPAULLONES FOR PREVENTING AND TREATING PANCREATIC AUTOIMMUNE DISORDERS

(75) Inventors: Rainer Mussmann, Göttingen (DE); Conrad Peter Kunick, Hamburg (DE); Hendrik Stukenbrock, Braunschweig (DE); Marcus Geese, Göttingen (DE); Simone Kegel, Uslar (DE); Ulrike Burk, Göttingen (DE)

(73) Assignees: Develogen Atkiengesellschaft, Goettingen (DE); Technische Universitaet Carolo-Wilhelmina Zu Braunschweig, Braunschweig (DE)

( * ) Notice: Subject to any disclaimer, the term of this patent is extended or adjusted under 35 U.S.C. 154(b) by 497 days.

(21) Appl. No.: 11/913,486

(22) PCT Filed: May 4, 2006

(86) PCT No.: PCT/EP2006/004186
§ 371 (c)(1),
(2), (4) Date: Jun. 3, 2008

(87) PCT Pub. No.: WO2006/117221
PCT Pub. Date: Nov. 9, 2006

(65) Prior Publication Data
US 2008/0287423 A1      Nov. 20, 2008

(30) Foreign Application Priority Data

| May 4, 2005 | (EP) | 05009846 |
| Jul. 22, 2005 | (EP) | 05015986 |
| Oct. 24, 2005 | (EP) | 05023168 |
| Jan. 23, 2006 | (EP) | 06001327 |

(51) Int. Cl.
*C07D 471/14* (2006.01)
*A61K 31/55* (2006.01)

(52) U.S. Cl. .................. 514/212.06; 540/521

(58) Field of Classification Search .................. 540/521; 514/212.06
See application file for complete search history.

(56) References Cited

U.S. PATENT DOCUMENTS

| 2003/0181439 A1 | 9/2003 | Meijer et al. |
| 2005/0090483 A1 | 4/2005 | Engler et al. |
| 2005/0171094 A1 | 8/2005 | Kataoka et al. |

FOREIGN PATENT DOCUMENTS

| EP | 1477490 A | 11/2004 |
| WO | WO 02/086107 A | 10/2002 |
| WO | WO 03/011843 A | 2/2003 |

OTHER PUBLICATIONS

Kunick et al. (Bioorganic & Medicinal Chemistry Letters (2004), 14(2), 413-416).*
Cohen Philip et al: "GSK3 inhibitors: development and therapeutic potential," Nature Reviews. Drug Discovery. Jun. 2004, vol. 3, No. 6, Jun. 2004, pp. 479-487, XP002357670 ISSN: 1474-1776.
Martinez A et al: "Glycogen synthase kinase 3 (GSK-3) inhibitors as new promising drugs for diabetes, neurodegeneration, cancer, and inflammation" Medicinal Research Reviews 2002 United States, vol. 22, No. 4, 2002, pp. 373-384, XP009058328 ISSN: 0198-6325.

* cited by examiner

*Primary Examiner* — Bruck Kifle
(74) *Attorney, Agent, or Firm* — Millen, White, Zelano & Branigan, P.C.

(57) ABSTRACT

This invention relates to the use of azapaullones, particularly in combination with immunomodulating agents, in the prevention, and/or treatment of pancreatic autoimmune disorders, e.g. type I diabetes or LADA and neurodegenerative disorders.

6 Claims, 17 Drawing Sheets

Fig. 10a
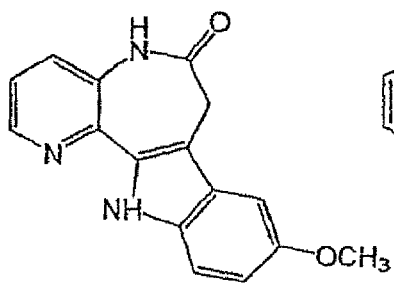
Chemical Formula: C₁₆H₁₃N₃O₂
Molecular Weight: 279,29
Fig. 10 b
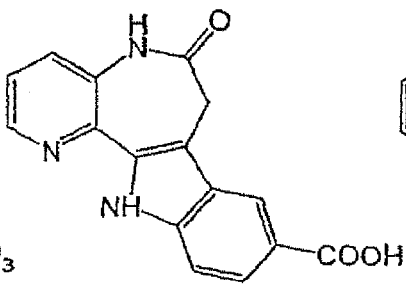
Chemical Formula: C₁₆H₁₁N₃O₃
Molecular Weight: 293,28
Fig. 10 c
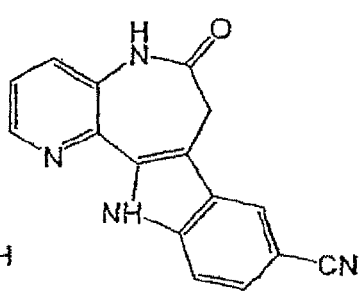
Chemical Formula: C₁₆H₁₀N₄O
Molecular Weight: 274,28
Fig. 10 d
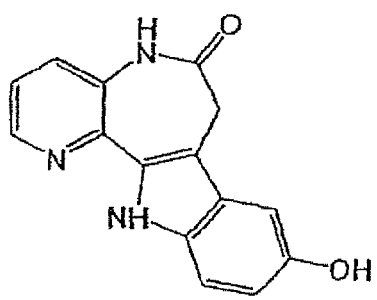
Chemical Formula: C₁₅H₁₁N₃O₂
Molecular Weight: 265,27
Fig. 10 e
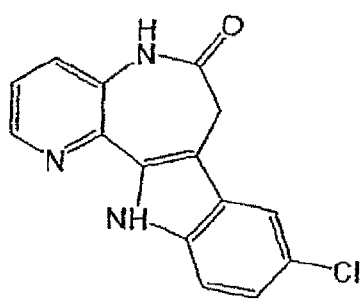
Chemical Formula: C₁₅H₁₀ClN₃O
Molecular Weight: 283,71
Fig. 10 f
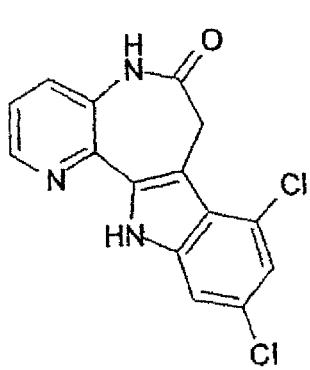
Fig. 10 g

|  | Reference: DG340002 (10 µM) | Test compound: 10c (10 µM) | Test compound: 10e (10 µM) |
|---|---|---|---|
| GSK3α(h) | 0 | 0 | -1 |
| GSK3β(h) | 4 | 1 | 3 |
| CDK1/cyclinB(h) | 52 | 33 | 55 |
| CDK2/cyclinA(h) | 49 | 2 | 53 |
| CDK2/cyclinE(h) | 68 | 6 | 62 |
| CDK5/p25(h) | 49 | 2 | 60 |
| CDK5/p35(h) | 60 | 2 | 52 |
| Lck(h) | 52 | 10 | 51 |
| MAPK1(h) | 91 | 78 | 72 |
| MAPK2/ERK2(h) | 97 | 88 | 87 |
| MAPKAP-K2(h) | 86 | 94 | 105 |
| MAPKAP-K3(h) | 91 | 84 | 99 |
| PKCα(h) | 106 | 92 | 104 |
| PKCδ(h) | 95 | 90 | 94 |
| PKCζ(h) | 85 | 74 | 82 |
| PDK1(h) | 89 | 83 | 93 |
| AMPK(r) | 112 | 100 | 107 |
| SAPK2a/p38(h) | 108 | 107 | 106 |
| SAPK3/γ(h) | 94 | 102 | 102 |
| CK2(h) | 43 | 33 | 59 |
| IR(h) | 92 | 94 | 90 |
| LIMK1(h) | 87 | 101 | 108 |
| PKA(h) | 107 | 105 | 104 |
| PRAK(h) | 87 | 84 | 86 |
| ROCK-II(h) | 78 | 72 | 84 |
| SGK(h) | 106 | 103 | 111 |
| CHK1(h) | 115 | 60 | 121 |
| EphB2(h) | 87 | 74 | 86 |

IC50's for GSK3
- Test compound 10c: 15 nM
- 1-Azapaullone: 17 nM

B

IC50's for CDK1/cyclinB
- Test compound 10c: 500 nM
- 1-Azapaullone: 22000 nM

USE OF AZAPAULLONES FOR PREVENTING AND TREATING PANCREATIC AUTOIMMUNE DISORDERS

DESCRIPTION

This invention relates to the use of azapaullones, particularly in combination with immunomodulating agents, in the prevention, and/or treatment of pancreatic autoimmune disorders, e.g. type I diabetes or LADA.

Pancreatic beta-cells secrete insulin in response to elevated blood glucose levels. Insulin amongst other hormones plays a key role in the regulation of the fuel metabolism. Insulin leads to the storage of glycogen and triglycerides and to the synthesis of proteins. The entry of glucose into muscles and adipose cells is stimulated by insulin. In patients who suffer from diabetes mellitus type I or LADA (latent autoimmune diabetes in adults, Pozzilli & Di Mario, 2001, Diabetes Care. 8:1460-67) beta-cells are being destroyed due to autoimmune attack. The amount of insulin produced by the remaining pancreatic islet cells is too low, resulting in elevated blood glucose levels (hyperglycemia). In diabetes mellitus type II liver, muscle and fat cells loose their ability to respond to normal blood insulin levels (insulin resistance). High blood glucose levels (and also high blood lipid levels) in turn lead to an impairment of beta-cell function and to an increase in beta-cell death. Interestingly the rate of beta-cell neogenesis and replication does not appear to increase in type II diabetics, thus causing a reduction in total beta-cell mass over time. Eventually the application of exogenous insulin becomes necessary in type II diabetics.

In type I diabetics, where beta-cells are being destroyed by autoimmune attack, treatments have been devised which modulate the immune system and may be able to stop or strongly reduce islet destruction (Raz et al., 2001, Lancet 358: 1749-1753; Chatenoud et al., 2003, Nat Rev Immunol. 3:123-132; Homann et al., Immunity. 2002, 3:403-15). However, due to the relatively slow regeneration of human beta-cells such treatments can only be successful if they are combined with agents that can stimulate beta-cell regeneration.

The combination of immunosuppressive or immunomodulatory agents with beta cell growth/regeneration factors strongly promotes the remission of overtly diabetes in female NOD mice, a mouse model for autoimmune diabetes, and leads to an at least partial restoration of pancreatic insulin content and to an improved glucose tolerance as demonstrated by the work of Ogawa and coworkers (Ogawa et al., 2004, Diabetes, 53:1700-1705), who combined anti-lymphocyte serum, an immunosuppressant, with the beta cell growth factor exendin-4, a long-acting form of glucagon-like peptide 1 (GLP-1). Gross and coworkers (Gross et al., 1998, Endocrinology, 139: 2369-2374) came to similar conclusions combining oral linomide (quinoline-3-carboxamide), a substance shown to prevent autoimmune insulitis, islet destruction, and diabetes in NOD mice treated at an early stage of the disease, with Reg protein, a protein with beta cell regenerative potential. The combination therapy is also under active investigation in a clinical phase II trial (ClinicalTrials.gov Identifier: NCT00064714) of the National Institute of Diabetes and Digestive and Kidney Diseases (NIDDK), USA. In this study the effects of exendin-4 administered in combination with daclizumab, a humanized mouse monoclonal antibody targeting the interleukine-2 receptor with immunosuppressive properties, on beta cell functions and disease progression of patients with type I diabetes are being investigated. Also in the field of islet transplantation where the gradual deterioration of beta cell function of transplanted islets poses a major challenge for the whole approach investigators consider to treat islet recipients with beta cell growth factors in addition to an immunosuppressive regimen which transplant recipient have to take anyway for the prophylaxis of islet rejection (Shapiro et al., 2005, Transplantation, 79:1304-1307).

Diabetes is a very disabling disease, because today's common anti-diabetic drugs do not control blood sugar levels well enough to completely prevent the occurrence of high and low blood sugar levels. Frequently elevated blood sugar levels are toxic and cause long-term complications like for example nephropathy, retinopathy, neuropathy and peripheral vascular disease. Extensive loss of beta cells also leads to deregulation of glucagon secretion from pancreatic alpha cells which contributes to an increased risk of dangerous hypoglycemic episodes. There is also a host of related conditions, such as obesity, hypertension, heart disease and hyperlipidemia, for which persons with diabetes are substantially at risk.

Apart from the impaired quality of life for the patients, the treatment of diabetes and its long term complications presents an enormous financial burden to our healthcare systems with rising tendency. Thus, for the treatment of diabetes mellitus type I and LADA, but also for the treatment of late stages of diabetes mellitus type II there is a strong need in the art to identify factors that induce regeneration of pancreatic insulin producing beta-cells. These factors could restore normal function of the endocrine pancreas once its function is impaired or event could prevent the development or progression of diabetes type I, LADA or late stage diabetes type II.

The technical problem underlying the present invention was to provide for means and methods for treating pancreatic autoimmune disorders, particularly autoimmune diabetes such as type I diabetes or LADA, but also late stage type II diabetes. The solution to said technical problems is achieved by providing the embodiments characterized in the claims.

We set out to identify new small molecules of the Azapaullone family of kinase inhibitors capable of activating the proliferation of pancreatic beta cells as well as protecting them against stress-induced cell death. The induction of Pax4 gene expression was chosen as a read out in the primary and secondary screening assays used in the course of the invention because the overexpression of Pax4 in human and rodent beta cells promotes beta cell proliferation and survival. Pax4 also promotes beta cell formation from stem cells in vitro and possibly neogenesis in vivo in Pax4-transgenic mice (see, for example, WO02/086107, U.S. Pat. Nos. 6,071,697, 5,948, 623, EP0958357, JP3631765, EP1288311, U.S. 60/600,704 which are incorporated herein by reference).

The present invention is based on the finding that compounds derived from the chemical families of the azapaullones stimulate the proliferation of INS-1E cells and protect them against glycolipotoxicity induced cell death.

The present invention is based on the finding that some of the above compounds stimulate the transcription of Pax4 in insulinoma INS-1E cells in vitro. An increased activity of the Pax4 gene stimulates proliferation and suppresses cell death in human beta cells. Pax4 can also stimulate beta cell formation from stem cells. The activity of Pax4 may be modulated through the effects of target molecules, e.g. GSK-3, on Pax4 activity. Inhibition or down-regulation of these target molecules results in increased Pax4 activity. Activation of Pax4 has been linked to diabetic disorders. Methods are also provided for enhanced regeneration of pancreatic beta cells through the action of the above compounds, when administered in conjunction with other immunosuppressive agents. Thus, these compounds have been identified in this invention as modulators of beta-cell regeneration.

The present invention relates to the use of a compound of formula (I), particularly in combination with an immunosuppressive agent for the manufacture of a medicament for the prevention and/or treatment of autoimmune pancreatic disorders, preferably for the prevention and/or treatment of autoimmune diabetes, more preferably for the prevention and/or treatment of type I diabetes or LADA, but also for type II late-stage diabetes.

The compounds of formula (Ia) are azapaullones

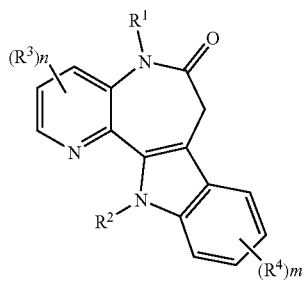

(Ia)

wherein R1 and R2 are independently H, —$C_1$-$C_6$ alkyl, optionally substituted, or —CO—$C_1$-$C_6$ alkyl, optionally substituted, wherein the substituents are independently selected from one or more of halo, CN, OH, O—$C_1$-$C_6$ alkyl; COOH, COO—$C_1$-$C_6$ alkyl, —CONH$_2$, —CONH($C_1$-$C_6$) alkyl, —CON($C_1$-$C_6$ alkyl)$_2$, aryl, heteroaryl, polyoxyethylenyl or combinations thereof;

each R3 and R4 is independently selected from $C_1$-$C_6$ alkyl, —$C_2$-$C_6$ alkenyl; —$C_2$-$C_6$ alkynyl; —$C_3$-$C_{10}$ cycloalkyl, —$C_3$-$C_{10}$ heterocyclyl, aryl with 6 to 10 carbon atoms, heteroaryl with 5 to 10 ring atoms;

each optionally substituted; halo, e.g. F, Cl, Br or I; —NO$_2$, —CN, —OR1; —COOR1 or —NR1R2; wherein R1 and R2 are as defined above; and wherein alkyl, alkenyl or alkynyl is optionally substituted with one or more of oxo, halo, —NO$_2$, —CN, —OR1, COOR1, —OCOR1, —NR1R2, NR1COR2, —NR1OCOR2, —NR1CONR1R2, —SR1, SOR1, —SO$_2$R1, —SONR1R2, SO$_2$NR1R2 or —NR1SO$_2$NR1NR2; or combinations thereof, wherein R1 and R2 are as defined above;

wherein cycloalkyl, heterocyclyl, aryl or heteroaryl is optionally substituted with one or more of $C_1$-$C_6$ alkyl, oxo, halo, —NO$_2$, —CN, —OR1, COOR1, —OCOR1, —NR1R2, NR1COR2, —NR1OCOR2, —NR1CONR1R2, —SR1, SOR1, —SO$_2$R1, —SONR1R2, SO$_2$NR1R2 or —NR1SO$_2$NR1NR2; or combinations thereof, wherein R1 and R2 are as defined above;

or wherein two R3 or two R4 may together form a ring;
n=0-3, preferably 0-1 and more preferably 0;
m=0-3, preferably 0, 1 or 2 and more preferably 1 or 2;
or an optical isomer or a salt thereof.

Preferably R1 and R2 are independently H, —$C_1$-$C_5$ alkyl, optionally halogenated or substituted with COO—$C_1$-$C_6$ alkyl such as CH$_2$—COO—CH$_3$, or CO—$C_1$-$C_5$ alkyl. More preferably R1 and R2 are H. Preferably each R3 and R4 is independently selected from $C_1$-$C_5$ alkyl, optionally halogenated such as CH$_3$ or CF$_3$, halo, —NO$_2$, —CN, —OR1, —COOR1, —OCOR1, —NR1NR2 and —NR1COR2. More preferably R4 is preferably selected from alkyl, haloalkyl, halo, e.g. F, Cl, Br or I; and —NO$_2$ and CN.

Especially preferred azapaullones are compounds of general formula (Ib) or (Ic):

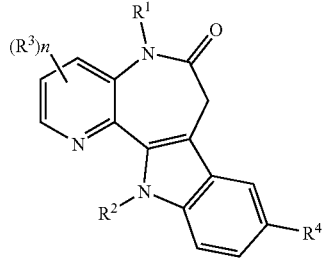

(Ib)

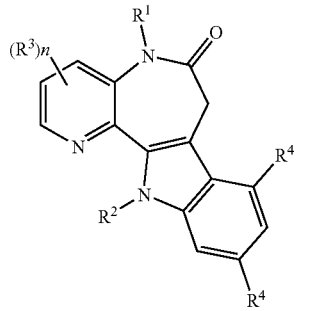

(Ic)

wherein R1, R2, R3, and R4 are defined as for the compounds of formula (Ia).

In the compounds (Ia), (Ib) and (Ic) the following substituents are preferred (either independently of each other or in combination):

R1 is H; or $C_1$-$C_2$ alkyl optionally substituted e.g. with COO—$C_1$-$C_6$ alkyl; preferably H;

R2 is H; or $C_1$-$C_2$ alkyl optionally substituted e.g. with COO—$C_1$-$C_6$ alkyl; preferably H;

n=1 and R3 is O—$C_1$-$C_4$-alkyl or O-aryl, or n=0,

R4 is R1' (wherein R1' is H or $C_1$-$C_4$ alkyl, optionally halogenated, e.g. methyl or trifluoromethyl), OR1' (wherein R1' is H or $C_1$-$C_4$ alkyl, optionally halogenated, e.g. methyl), COOR1" (wherein R1" is H, $C_1$-$C_4$ alkyl or aryl), CN, or halo, e.g. Cl; and preferably CN.

Particularly preferred examples of suitable azapaullones are 4-Azakenpaullone and compounds as shown in FIG. 10a-m. Most preferred are compounds 10c, 10e and 10l.

Pharmaceutically acceptable addition salts of the above compounds (Ia) and (Ib), and (Ic) include but are not limited to salts with physiologically acceptable cations or anions. Examples of cations are alkaline earth metals such as sodium, lithium, potassium, calcium, magnesium, aluminium salts or the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylene diamine, ethanolamine, diethanolamine, piperazine and the like and salts with amino acids such as arginine, lysine or the like. Examples of anions are inorganic anions such as chloride, sulphate, hydrogen sulphate, phosphate, hydrogen phosphate etc. and organic anions, e.g. carboxylate, sulphate or sulphonate anions such as acetate, lactate, tartrate, tosylate, mesylate etc.

The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

The invention also relates to metabolites and prodrugs. As used herein, the term "metabolite" refers to (i) a product of metabolism, including intermediate and products, (ii) any substance in metabolism (either as a product of metabolism or as necessary for metabolism), or (iii) any substance produced or used during metabolism. In particular it refers to the end product that remains after metabolism. As used herein the term "prodrug" refers to (i) an inactive form of a drug that exerts its effects after metabolic processes within the body converts it to a usable or active form, or (ii) a substance that gives rise to a pharmacologically active metabolite, although not itself active (i.e. an inactive precursor).

As used herein the term "$C_3$-$C_{10}$ cycloalkyl" refers to mono- or polycyclic saturated or unsaturated carbocyclic alkyl groups such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl and cycloheptatrienyl and the like.

The terms "alkyl" and "alkoxy" are used herein or in combination with other terms refer to a $C_1$-$C_6$, preferably $C_1$-$C_5$ straight or branched alkyl/alkoxy group such as methyl, ethyl, propyol (iso-, n-), butyl (iso-, n-, tert-), pentyl, hexyl, methoxy, ethoxy, propoxy (iso-, n-), butoxy (iso-, n-, tert-), pentoxy, hexoxy.

The term "halogen" refers to a halogen atom selected from fluorine, chlorine, bromine, iodine, preferably fluorine and chlorine, more preferably fluorine.

The term "aryl" refers to mono- and polycyclic aromatic groups having 6 to 10 backbone carbon atoms, optionally fused to a carbocyclic group, such as phenyl, 1-naphthyl, indenyl, indanyl, azulenyl, fluorenyl, 1,2,3,4-tetrahydronaphthyl, etc.

The term "heterocyclyl" refers to mono- or polycyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperadinyl, pyridyl, pyrimidinyl, triazolyl, indolyl, imidazolyl, oxadiazolyl, tetrazolyl, pyrazinyl, triazolyl, thiophenyl, furanyl, indazolyl, pyrazolopyrimidinyl, quinazolyl, etc.

The term "heteroaryl" refers to mono- or bicyclic aromatic groups with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolynyl, purinyl, carbazolyl, benzoxazolyl, benzamidazolyl, indolyl, isoindolyl, pyrazinyl, diazinyl, triazinyltriazine, tetrazinyl, tetrazolyl, or benzimidazolyl.

The term "polyoxyethylenyl" refers to groups containing at least 2, e.g. 2-50 oxyethylenyl (—$OCH_2$—$CH_2$—) groups, such as polyoxyethylenyloxycarbonyl or polyoxyethylenylaminocarbonyl groups. Polyoxyethylenyl groups are preferably present at position $R^2$, e.g. $R^1$ is H and $R^2$ is polyoxyethylenyl.

The novel azapaullones may be prepared by thermal Fischer indolization reactions from appropriate phenyl hydrazones. These precursors are synthesized from an appropriate commercially available phenyl hydrazine and 5H-pyrido[3,2-b]azepine-6,9(7H,8H)-dione, which is prepared following a method published by Kunick et al. (C. Kunick, K. Lauenroth, M. Leost, L. Meijer, T. Lemcke: *Bioorg. Med. Chem. Lett.* 2004, 14, 413-416). The thermal Fischer indolization is conventionally performed by refluxing the phenyl hydrazone in diphenyl ether. In contrast, the new azapaullone 10a is available by refluxing the precursor in ethanol. Furthermore, it was demonstrated for the new azapaullone 10c that the thermal Fischer indolization leading to paullones may alternatively be performed by heating a phenyl hydrazone precursor in water in a dedicated microwave device.

The compounds of the invention are considered to be mitogens and/or beta cell protective agents capable of promoting the protection, survival and/or regeneration of insulin producing cells, particularly pancreatic beta cells. In addition, the compounds also may suppress apoptotic events in beta cells thereby preventing beta cell loss. In addition, by inducing Pax4 these compounds may support beta cell neogenesis from stem or progenitor cells in vitro and in vivo.

Further, novel compounds of the present invention are suitable as agents for the prevention or treatment of neurodegenerative disorders such as Alzheimer's disease and other tautopathies, Huntington's disease, bipolar disorders, e.g. manic-depressive illness, Parkinson's disease, MS, ALS and other diseases, e.g. GSK3-associated diseases such as described in Kypta (Expert Opin. Ther. 15 (2005), 1315-1331), Cohen and Goedert (Nature (June 2004, Vol. 3), 479-487), Meijer et al. (Trends Pharmacol. Sci. (2004), 471-480), WO 2005/039485 and Trowbridge et al. (Nat. Med. 12 (2006), 89-98) and references cited therein which are herein incorporated by reference.

The compounds may be administered alone or in combination with other medicaments. For example, the compounds may be administered with a further medicament useful to prevent or treat pancreatic disorders or metabolic syndrome, particularly beta-cell degeneration, e.g. known beta cell mitogens and/or beta cell protective agents. Further medicaments may be selected from activins, e.g. activin A, activin B and/or activin AB, hormones, growth factors such as prolactin or NGF, or antioxidants such as GLP-1 and stabilized forms of GLP-1, GLP-1 analogues, DPP-IV inhibitors, nicotinamide, vitamin C, INGAP peptide, TGF-alpha, gastrin, prolactin, members of the EGF-family, or immune modulating agents such as anti-CD3 antibodies, DiaPep277 or anti-inflammatory agents such as Cox2 inhibitors, acetyl-salicylic acid, or acetaminophen. The compounds may also be administered in combination with the beta cell regenerating proteins, e.g. secreted factors, nucleic acids and effectors/modulators thereof described in PCT/EP2004/003244, PCT/EP2004/003417, PCT/EP2004/007531, PCT/EP2004/007916, PCT/EP2004/007917, e.g. pleiotrophin and agonists thereof, PCT/EP2004/013175, PCT/EP2004/013535, PCT/EP 2005/000545, PCT/EP 2005/0017111 and PCT/EP/2005/008578, which are herein incorporated by reference. Other suitable medicaments include neurturin products as described in PCT/EP2004/013534, herein incorporated by reference, and other members of the GDNF/neurturin family of growth factors, VitD3 and analogous thereof, gastric inhibitory polypeptide (GIP) and analogous thereof, insulin growth factor (IGF) I or II and analogues thereof, growth hormone (GH) and analogues thereof, placental lactogen (PL) or analogues thereof, hepatic growth factor (HGF) or analogue thereof, betacelullin or analogues thereof, parathyroid hormone related protein and analogues thereof (PTHrP), insulin and analogues thereof, fibroblast growth factors (FGFs) and analogues thereof, cholecystokinin (CCK) and analogues thereof, and peroxisome proliferator-activated receptor (PPAR) agonists such as thiazolidinediones (TZDs).

The compounds preserve beta cell mass and/or leads to a net increase in beta cell mass. Therefore, the compounds may be used for the prevention, amelioration and/or treatment of pancreatic autoimmune disorders, that are associated with beta cell loss.

Treatment in a medical setting could mean the direct application to patients for instance by injection. In the context of islet transplantation the agent may be used to promote survival and growth as well as differentiation of donor duct cells and islets in culture prior to or after their transfer into recipients. Another use is in stem cell differentiation protocols aiming to the production of beta cell-like cells in culture. The agent can act as a maturation factor promoting the differentiation of stem cells towards the pancreatic lineage or promoting the growth of differentiated cells.

Thus, the present invention provides methods for treating patients suffering from a pancreatic autoimmune disease caused by, associated with, and/or accompanied by functionally impaired and/or reduced numbers of pancreatic islet cells, particularly insulin producing beta-cells, by administering a therapeutically effective amount of compositions as indicated above. Functional impairment or loss of pancreatic islet cells may be due to e.g. autoimmune attack such as in diabetes type I or LADA, and/or due to cell degeneration such as in progressed diabetes type II. The methods of the present invention may also be used to treat patients at risk to develop degeneration of insulin producing beta-cells to prevent the start or progress of such process.

Numerous additional aspects and advantages of the invention will become apparent to those skilled in the art upon consideration of the following detailed description of the invention which describes presently preferred embodiments thereof.

In connection with the present invention, the term "progenitor cells" relates to undifferentiated cells capable of being differentiated into insulin producing cells. The term particularly includes stem cells, i.e. undifferentiated or immature embryonic, adult, or somatic cells that can give rise to various specialized cell types. The term "stem cells" can include embryonic stem cells (ES) and primordial germ (EG) cells of mammalian, e.g. human or animal origin. Isolation and culture of such cells is well known to those skilled in the art (see, for example, Thomson et al., (1998) Science 282: 1145-1147; Shamblott et al., (1998) Proc. Natl. Acad. Sci. USA 95: 13726-13731; U.S. Pat. Nos. 6,090,622; 5,914,268; WO 00/27995; Notarianni et al., (1990) J. Reprod. Fert. 41: 51-56; Vassilieva et al., (2000) Exp. Cell. Res. 258: 361-373). Adult or somatic stem cells have been identified in numerous different tissues such as intestine, muscle, bone marrow, liver, and brain. WO 03/023018 describes a novel method for isolating, culturing, and differentiating intestinal stem cells for therapeutic use. In the pancreas, several indications suggest that stem cells are also present within the adult tissue (Gu and Sarvetnick, (1993) Development 118: 33-46; Bouwens, (1998) Microsc Res Tech 43: 332-336; Bonner-Weir, (2000) J. Mol. Endocr. 24: 297-302).

Embryonic stem cells can be isolated from the inner cell mass of pre-implantation embryos (ES cells) or from the primordial germ cells found in the genital ridges of post-implanted embryos (EG cells). When grown in special culture conditions such as spinner culture or hanging drops, both ES and EG cells aggregate to form embryoid bodies (EB). EBs are composed of various cell types similar to those present during embryogenesis. When cultured in appropriate media, EB can be used to generate in vitro differentiated phenotypes, such as extraembryonic endoderm, hematopoietic cells, neurons, cardiomyocytes, skeletal muscle cells, and vascular cells. We have previously described a method that allows EB to efficiently differentiate into insulin-producing cells (as described in WO 02/086107 and by Blyszczuk et al., (2003) Proc Natl Acad Sci USA 100: 998-1003), which are incorporated herein by reference.

In the present invention the term "beta-cell regeneration" refers to an at least partial restoration of normal beta-cell function by increasing the number of functional insulin secreting beta-cells and/or by restoring normal function in functionally impaired beta-cells.

Before the present invention is described in detail, it is understood that all technical and scientific terms used herein have the same meanings as commonly understood by one of ordinary skill in the art to which this invention belongs.

The data disclosed in this invention show that the compositions of the invention are useful in diagnostic and therapeutic applications implicated, for example, but not limited to, pancreatic autoimmune disorders. Hence, diagnostic and therapeutic uses for the compositions of the invention of the invention are, for example but not limited to, the following: (i) tissue regeneration in vitro and in vivo (regeneration for all these tissues and cell types composing these tissues and cell types derived from these tissues), (ii) small molecule drug target, (iii) antibody target (therapeutic, diagnostic, drug targeting/cytotoxic antibody), (iv) diagnostic and/or prognostic marker, (v) protein therapy, (vi) gene therapy (gene delivery/gene ablation), and (vii) research tools.

According to this invention the composition may be administered i) as a pharmaceutical composition e.g. enterally, parenterally or topically, preferably directly to the pancreas and/or ii) via implantation of treated cells.

Compositions as indicated above, preferably refer to compositions comprising an active compound (Ia, Ib) optionally in combination with a further medicament, as described above.

More particularly, the compositions may be administered together with beta cell mitogens and/or beta cell protective agents such as GLP-1 or derivatives thereof such as GLP-1 or derivatives thereof, e.g. GLP-1 (7-36 amide), exendin-4, prolactin or neurotrophins such as NGF.

The compositions are preferably administered together with pharmaceutical agents which have an immunosuppressive activity, e.g. antibodies, polypeptides and/or peptidic or non-peptidic low molecular weight substances.

Preferred examples of immunosuppressive agents are listed in the following Table 1.

TABLE 1

Exemplary agents for immune suppression

| Names | Mechanisms |
| --- | --- |
| 2-amino-1,3-propanediol derivatives | Used for preventing or treating chronic rejection in a patient receiving an organ or tissue allo- or xenotransplant |
| 2-amino-2[2-(4-octylphenyl)ethyl]propane-1,3-diol hydrochloride | Immunosuppression, from accelerated lymphocyte homing |
| 4-thiophenoxy-n-(3,4,5-trialkoxyphenyl) pyrimidine-2-amines | Lck inhibitors |
| 40-O-(2-hydroxyethyl)-rapamycin, SDZ-RAD, Everolimus | Sirolimus (rapamycin) derivative, used for acute kidney rejection; reduces rejection and graft vasculopathy following heart transplantation by inhibiting cell proliferation |
| 6-(3-dimethyl-aminopropionyl) forskolin | Immunosuppressing action useful also for treating autoimmune disease |
| 6-mercaptopurine (6-MP) | Used to treat Crohn's disease, inflammatory bowel disease and for organ transplant therapy |
| A-420983 | Lck-inhibitor |
| ABX-CBL (CBL-1) | Mouse monoclonal AB targeted against human T-cell, B-cells, NK-cells and monocytes, for treatment of steroid-resistant graft-vs-host diseases, potential use in treatment of inflammatory and autoimmune disorders |
| Alefacept (human LFA-3 IgG1 fusion protein) | Knocks out causative memory T-lymphocytes; used to treat psoriasis, a T-cell mediated inflammatory disorder |
| Antisense ICAM-1 inhibitor (ISIS 2302), Enlimomab, BIRR1, Alicaforsen | Mouse monoclonal AB blocks white blood cell adhesion to T-cell surface molecule (ICAM-1r); treatment of kidney transplant rejection |
| Antithymocyte immunoglobulin (ATGAM) | Anti-human thymocyte, immunoglobulin; used in reversal of acute kidney transplant rejection and will likely be used off-label for transplant induction therapy |
| Azathioprine | Treatment of rheumatoid arthritis and prevention of kidney transplant rejection, and other autoimmune or inflammatory disorders such as inflammatory bowel disease |
| Baohuoside-1 | Flavonoid; inhibits lymphocyte activation; Ma et al.. Transplantation 78: 831-838, (2004) |
| basiliximab | Monoclonal AB that binds to receptor sites on T-cells, preventing activation by transplanted tissue (renal transplant) |
| BMS-279700 | Lck-inhibitor |
| BTI-322 | Mouse derived monoclonal AB targeted to CD2 receptor; used for prevention of first-time kidney rejection, and treatment of resistant rejection |
| Cladribine | Antimetabolite and immunosuppressive agent that is relatively selective for lymphocytes; used to treat lymphoid malignancies, e.g. hairycell leukemia |
| CP-690550 | JAK-3 inhibitor |
| Cyclophosphamide (CTX) | Immunosuppressant for treatment of arthritis and other auto-immune disorders and cancers |
| Cyclosporine (cyclosporin A, cyclosporin) | 11 amino acid cyclic peptide; blocks helper T-cell, immunosuppressant used in organ transplant therapy and other immune diseases |
| Daclizumab, HAT (Humanized Anti-Tac), SMART anti-Tac, anti-CD25, and humanized anti-IL2-receptor | Monoclonal AB inhibits binding of IL-2 to IL-2 receptor by binding to IL-2 receptor; suppresses T-cell activity against allografts (renal transplant) |
| Dexamethasone (Decadron, Dexone, Dexasone) | An adrenocorticoid, effective immunosuppressant in various disorders |
| DIAPEP-277 | Immunomodulatory properties |
| DiaMyd peptide | GAD-derived immunomodulatory peptide |
| Dipeptide Boronic Acid (DPBA) | Proteasome inhibitor; Wu et al., Transplantation 78: 360-366, (2004) |
| Docosahexaenoic acid (DHA) | Immunosuppressant that lowers the proportion of T-cells expressing CD4 or CD8, blocks antigen recognition process; Taku et al., Journal of Agricultural and Food Chemistry 48: 1047, (2000) |

TABLE 1-continued

Exemplary agents for immune suppression

| Names | Mechanisms |
|---|---|
| efalizumab | T-cell modulator that target T-cells through interactions with adhesion molecules on endothelial cell surface, target migration of T-cells into the skin and target activation of T-cells; used to treat Psoriasis |
| Efomycine M | Leukocyte adhesion inhibitor, Anti-inflammatory |
| FTY720 (oral myriocin derivative) | Alters lymphocyte infiltration into grafted tissues; used for prevention of organ rejection in kidney transplants |
| GAD-based vaccine/immunemodulator, e.g. from Diamyd company | Prevention and treatment of insulin-dependent diabetes |
| Glatiramer acetate (co-polymer-1) | Synthetic peptide copolymer; decoy that mimics structure of myelin so immune cells bind Copaxone instead of myelin; for multiple sclerosis |
| Glial fibrillary acidic protein (GFAP) | Possesses immunosuppressive activities in diabetic animal models; Winer et al., Nature Medicine 9: 198, (2003) |
| Gusperimus (15-deoxyspergualin) | Intravenous immunosuppressant; suppresses production of cytotoxic T-cells, neutrophils and macrophages |
| HLA-B2702 peptide | Human peptide, blocks action of NK cells and T-cell mediated toxicities, used for prevention of first kidney allograft rejection |
| hu1124(anti-CD11a) | Humanized monoclonal antibody; targets CD11a receptor on surface of T-cells to selectively inhibit immune system rejection of transplanted organs |
| hOKT31gamma (Ala-Ala) | Non Fc-binding humanized anti CD3 antibody |
| IBC-VSO1 | A synthetic, metabolically inactive form of insulin designed to prevent pancreatic beta cell destruction (vaccine) |
| IGRP-derived peptides | T-cell modulator |
| Imatinib (STI571, Glivec or Gleevec) | Lck inhibitor |
| Infliximab | Monoclonal AB, binds and inactivates human TNFalpha; used to treat Crohn's disease and rheumatoid arthritis |
| Interferon | Immunomodulatory properties |
| ISAtx247 | Used to treat autoimmune diseases such as rheumatoid arthritis and psoriasis |
| Isotretinoin | Immunosuppressant, reduces ability of T-cells to proliferate in response to immune challenge. Vergelli et al., Immunopharmacology, 31: 191, (1997) |
| L-683,742: also described as 31-desmethoxy-31-hydroxy-L-683,590 | Treatment of autoimmune diseases, infectious diseases and/or prevention of organ transplant rejections |
| Leflunomide (ARAVA) | Antiinflammatory agent |
| Medi-500 (T10B9) | Intravenous monoclonal AB that targets human T-cells; treats acute kidney rejection and graft-vs-host disease |
| Medi-507 | Intravenous humanized AB directed against CD2 T-cell; used to treat corticosteroidresistant graft-vs-host disease and prevention of kidney rejection |
| Methotrexate | Antimetabolite used to treat Crohn's disease, severe psoriasis, and adult rheumatoid arthritis (and as an anti-cancer drug) |
| Mitoxantrone | Antiproliferative effect on cellular immune system including T-cells, B-cells and macrophages; used to treat hormone-refractory prostate cancer, acute myelogenous leukemia and multiple sclerosis |
| Mycophanclate mofetii | Inhibition of proliferation of T and B lymphocytes by blocking the synthesis of purine nucleotides; used in organ transplant therapy and inflammatory bowel disease |
| OKT4A | Mouse monoclonal AB targeted against human CD4 T-cell; used for prevention of kidney transplant rejection when used in combination with other immunosuppressant drugs |
| Oral interferon-alpha (IFN-alpha) | Early onset type 1 diabetes |

TABLE 1-continued

Exemplary agents for immune suppression

| Names | Mechanisms |
| --- | --- |
| Muromonab-CD3 | Monoclonal AB that binds to receptor sites on T-cells; preventing activation by transplanted tissue |
| Prednisolone | Corticosteroid, suppresses inflammation associated with transplant rejection |
| Psora-4 | Kv1.3-blocker |
| Rifampicin | Antibiotic; has immunomodulatory properties |
| Rituximab | CD20 antibody |
| S100beta | Possesses immunosuppressive activities in diabetic animal models |
| Sirolimus, Rapamycin | Immunosuppressant and potent inhibitor of cytokine (e.g. IL-2)-dependent T-cell proliferation (kidney transplant) |
| Tacrolimus (Prograf; FK-506) | Interferes with IL-2 TCR communication |
| Campath-1H | anti-CD52 monoclonal antibody |
| alpha-Galactosylceramide | Activation of NK-cells, immunomodulator |
| Linomide | Immunomodulator |
| Laquinimod (ABR-215062) | Linomide-derivative; immunomodulator |
| Lisofylline | antiinflammatory agent |

Preferred immunosuppressive agents are DiaPep277, anti-CD3-antibodies such as hOKT31 gamma (Ala-Ala) and GAD peptides such as DiaMyd GAD peptides.

The combination therapy may comprise coadministration of the medicaments during the treatment period and/or separate administration of single medicaments during different time intervals in the treatment period.

The compositions may be administered in patients suffering from a disease going along with reduced beta cell number and/or impaired beta-cell function, for example but not limited to one of the diseases for which a pro-proliferative effect on pancreatic beta cells and/or an anti-apoptotic/pro-survival effect on pancreatic beta cells and/or a beta cell neogenesis-promoting effect would be beneficial:

Type I diabetes: new onset, established, prevention in high-risk patients (identified e.g. via screening for multiple autoantibodies)
LADA: new onset and established
Type II diabetes: when loss of beta cell mass occurs
MODY (Maturity Onset Diabetes of the Young, all forms)
Gestational diabetes
Islet+duct cell transplantation–treatment of recipients before or after transplantation
Treatment of islets before transplantation/during pre-transplantation culture
Pancreatitis-associated beta cell loss The compositions are also useful for in vitro and ex vivo applications for which a pro-differentiation effect on pancreatic beta cells and precursors thereof would be beneficial:

In vitro differentiation of stem cells into beta cells
In vitro transdifferentiation of duct or exocrine cells into beta cells
MODY (all forms)
Persistent Hyperinsulinemic Hypoglycemia of Infancy More particularly, the compositions may be administered in diabetes type I, LADA or prognosed diabetes type II, but also preventively to patients at risk to develop complete beta-cell degeneration, like for example but not limited to patients suffering from diabetes type II or LADA and type I diabetes in early stages, or other types of diseases as indicated above. The compositions may also be used to prevent or ameliorate diabetes in patients at risk for type I diabetes or LADA (identified e.g. by screening for autoantibodies, genetic predisposition, impaired glucose tolerance or combinations thereof).

A variety of pharmaceutical formulations and different delivery techniques are described in further detail below.

The present invention also relates to methods for differentiating progenitor cells into insulin-producing cells in vitro comprising (a) activating one or more pancreatic genes in a progenitor, e.g. stem cell (optional step, particularly if embryonic stem cells are used)
(b) aggregating said cells to form embryoid bodies (optional step, particularly if embryonic stem cells are used)
(c) cultivating embryoid bodies or cultivating adult stem cells (e.g., duct cells, duct-associated cells, nestin-positive cells) in specific differentiation media containing a composition as indicated above under conditions wherein beta-cell differentiation is significantly enhanced, and
(d) identifying and selecting insulin-producing cells.

Activation of pancreatic genes may comprise transfection of a cell with pancreatic gene operatively linked to an expression control sequence, e.g. on a suitable transfection vector, as described in WO 03/023018, which is herein incorporated by reference. Examples of preferred pancreatic genes are Pdx1, Pax4, Pax6, neurogenin 3 (ngn3), Nkx 6.1, Nkx 6.2, Nkx 2.2, HB 9, BETA2/Neuro D, Isl 1, HNF1-alpha, HNF1-beta and HNF3 of human or animal origin. Each gene can be used individually or in combination with at least one other gene. Pax4 is especially preferred.

Further, the compositions are useful for the modulation, e.g. stimulation, of pancreatic development and/or for the regeneration of pancreatic cells or tissues, e.g. cells having exocrine functions such as acinar cells, centroacinar cells and/or ductal cells, and/or cells having endocrinous functions, particularly cells in Langerhans islets such as alpha-, beta-, delta- and/or PP-cells, more particularly beta-cells.

In a preferred embodiment, the composition and optionally an immuno-suppressive agent, can be delivered directly to progenitor, e.g. stem cells in order to stimulate the differentiation of insulin producing cells.

Further, the invention relates to a cell preparation comprising differentiated progenitor cells, e.g. stem cells exhibiting insulin production, particularly an insulin-producing cell line obtainable by the method described above. The insulin-producing cells may exhibit a stable or a transient expression of at least one pancreatic gene involved in beta-cell differentiation. The cells are preferably human cells that are derived from human stem cells. For therapeutic applications the production of autologous human cells from adult stem cells of a patient is especially preferred. However, the insulin producing cells may also be derived from non-autologous cells. If necessary, undesired immune reactions may be avoided by encapsulation, immunosuppression and/or modulation or due to non-immunogenic properties of the cells.

The insulin producing cells of the invention preferably exhibit characteristics that closely resemble naturally occurring beta-cells. Further, the cells of the invention preferably are capable of a fast response to glucose. After addition of 27.7 mM glucose, the insulin production is enhanced by a factor of at least 2, preferably by a factor of at least 3. Further, the cells of the invention are capable of normalizing blood glucose levels after transplantation into mice.

The invention further encompasses functional pancreatic cells obtainable or obtained by the method according to the invention. The cells are preferably of mammalian, e.g. human origin. Preferably, said cells are pancreatic beta-cells, e.g. mature pancreatic beta-cells or stem cells differentiated into pancreatic beta-cells. Such pancreatic beta cells preferably secrete insulin in response to glucose. Moreover, the present invention may provide functional pancreatic cells that secrete glucagon in response to hypoglycemia. A preparation comprising the cells of the invention may additionally contain cells with properties of other endocrine cell types such as delta-cells and/or PP-cells. These cells are preferably human cells.

The cell preparation of the invention is preferably a pharmaceutical composition comprising the cells together with pharmacologically acceptable carriers, diluents and/or adjuvants. The pharmaceutical composition is preferably used for the treatment or prevention of pancreatic diseases, e.g. diabetes.

According to the present invention, the functional insulin producing cells treated with compositions of the invention may be transplanted preferably intrahepatic, directly into the pancreas of an individual in need, or by other methods. Alternatively, such cells may be enclosed into implantable capsules that can be introduced into the body of an individual, at any location, more preferably in the vicinity of the pancreas, or the bladder, or the liver, or under the skin. Methods of introducing cells into individuals are well known to those of skill in the art and include, but are not limited to, injection, intravenous or parenteral administration. Single, multiple, continuous or intermittent administration can be effected. The cells can be introduced into any of several different sites, including but not limited to the pancreas, the abdominal cavity, the kidney, the liver, the celiac artery, the portal vein or the spleen. The cells may also be deposited in the pancreas of the individual.

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al., Winn et al., Exper. Neurol., 1 13:322-329, 1991, Aebischer et al., Exper. Neurol., 11 1:269-275, 1991; Tresco et al., ASAIO, 38: 17-23, 1992, each of which is specifically incorporated herein by reference. Techniques for formulating a variety of other sustained- or controlled-delivery means, such as liposome carriers, bio-erodible particles or beads and depot injections, are also known to those skilled in the art.

Immunomodulating medicaments, e.g. immunosuppressive drugs, such as cyclosporin, are preferably administered to the patient in need to reduce the host reaction versus graft. Allografts using the cells obtained by the methods of the present invention are also useful because a single healthy donor could supply enough cells to regenerate at least partial pancreas function in multiple recipients.

Administration of the pharmaceutical compositions to a subject in need thereof, particularly a human patient, leads to an at least partial regeneration of pancreatic cells. Preferably, these cells are insulin producing beta-cells that will contribute to the improvement of a diabetic state. With the administration of this composition e.g. on a short term or regular basis, an increase in beta-cell mass can be achieved. This effect upon the body reverses the condition of diabetes partially or completely. As the subject's blood glucose homeostasis improves, the dosage administered may be reduced in strength. In at least some cases further administration can be discontinued entirely and the subject continues to produce a normal amount of insulin without further treatment. The subject is thereby not only treated but could be cured entirely of a diabetic condition. However, even moderate improvements in beta-cell mass can lead to a reduced requirement for exogenous insulin, improved glycemic control and a subsequent reduction in diabetic complications.

Preferably, the compositions of the invention are intended for pharmaceutical applications and may comprise with a pharmaceutically acceptable carrier, for any of the therapeutic effects discussed above. Such pharmaceutical compositions may consist of the active ingredient of the invention. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means.

In addition to the active ingredients, these pharmaceutical compositions may contain suitable pharmaceutically-acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing Co., Easton, Pa.).

Pharmaceutical compositions suitable for use in the invention include compositions wherein the active ingredients are contained in an effective amount to achieve the intended purpose. The determination of an effective dose is well within the capability of those skilled in the art. For any compound, the therapeutically effective dose can be estimated initially either in cell culture assays, e.g., of pancreatic cells or in animal models, usually mice, rabbits, dogs or pigs. The animal model may also be used to determine the appropriate concentration range and route of administration. Such information can then be used to determine useful doses and routes for administration in humans. A therapeutically effective dose refers to that amount of active ingredient, which is sufficient for treating a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week or once every two weeks depending on half-life and clearance rate of the particular formulation. Normal dosage amounts may vary from 0.1 to 100,000 μg, up to a total dose of about 1 g, depending upon the route of administration. Guidance as to particular dosages and methods of delivery is provided in the literature and generally available to practitioners in the art.

The figures illustrate the invention:

FIG. 1 shows the proliferation rate of INS-1E cells treated with 4-Azakenpaullone (4AKP) relative to untreated controls. The proliferation rate of Ins-1E cells was determined by monitoring DNA synthesis using a 5-bromo-2'-deoxyuridine (BrdU) incorporation assay. BrdU is a halogenated nucleotide analogue of thymidine that is incorporated into DNA during the S-phase of the cell cycle. Pulse-labeling of DNA with BrdU and subsequent immunohistochemical detection of labeled nuclei was used to study the rate of cell proliferation. The treatment of INS-1E cells with 4-Azakenpaullone for 24 hours increases BrdU incorporation of Ins-1E cells in a concentration dependent manner, reaching a maximum of about 1.4 fold between 5 μM and 10 μM 4-AKP.

FIG. 2 shows the effect of 4-AKP on glucolipotoxicity induced apoptosis (referred to as "pal/gluc"; black line and triangle) of INS-1E cells compared to control INS-1E cells (referred to as "not ind", light grey line and rhombus). The effects of the substance on cell viability, cell growth and specific apoptotic events such as caspases activity and DNA-fragmentation was monitored. INS-1E cell apoptosis was induced by treatment of cell cultures with toxic concentrations of glucose and palmitate for 24 hours. The substance of interest was added to the medium 1 hour prior to the addition of the toxic agents.

Figure 2:
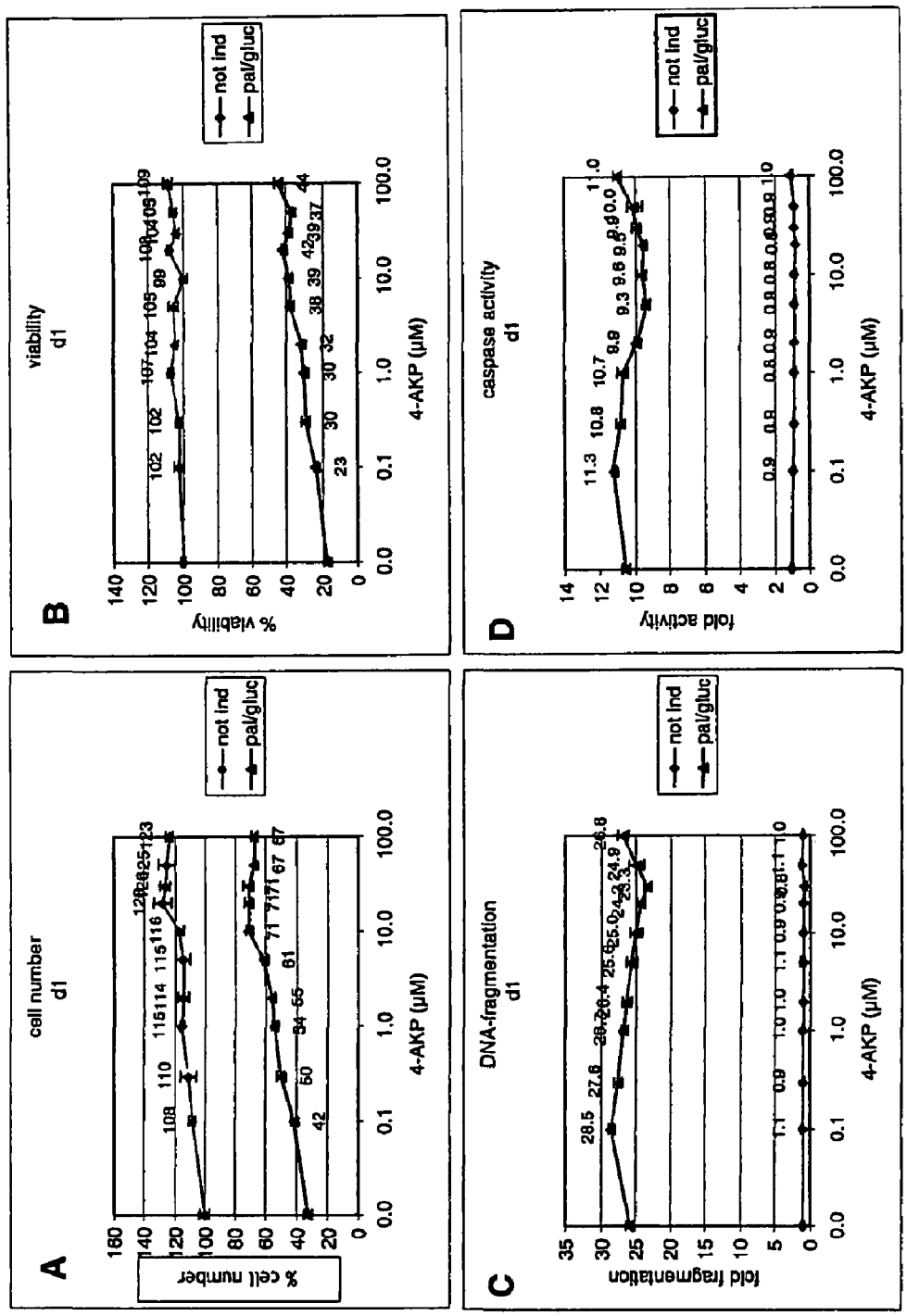
FIG. 2A shows that the treatment of INS-1E cells with 4-AKP for 24 hours results in a 1.2 fold increase in cell-number relative to untreated controls. The relative cell number was measured using the CyQuant assay as described under Example 3.
FIG. 2B shows that the treatment of INS-1E cells with 4-AKP slightly improves the viability of Ins-1E cells subjected to apoptosis inducing concentrations of glucose and palmitate. Viability was assessed by mitochondric reduction of the non toxic dye Alamar Blue.

FIG. 2C shows that 4-AKP slightly antagonizes apoptotic processes in INS-1E cells. DNA-fragmentation is a comparatively late apoptotic event comprising storage of nucleosomal DNA-fragments as mono- and oligo nucleosomes in the cytoplasm. The incubation of INS1-E cells with high concentrations of glucose and palmitate for 24 hours leads to DNA breakdown and the accumulation of nucleosomal DNA fragments in the cytoplasm. The detectable amount of cytosolic nucleosomal DNA fragments was reduced by about 17%, when cells were treated with the apoptosis inducing agents in combination with 10 μM 4-AKP.

FIG. 2D shows that the treatment of glucose/palmitate stressed INS-1E cells with 10 μM 4-AKP also reduces caspase activity by 18%. Caspase activation is a characteristic of early apoptotic cells. The experiment was carried out as described above with the exception that the caspases activity assay was applied instead of the DNA-fragmentation assay (see Example 3 for details).

Figure 1:
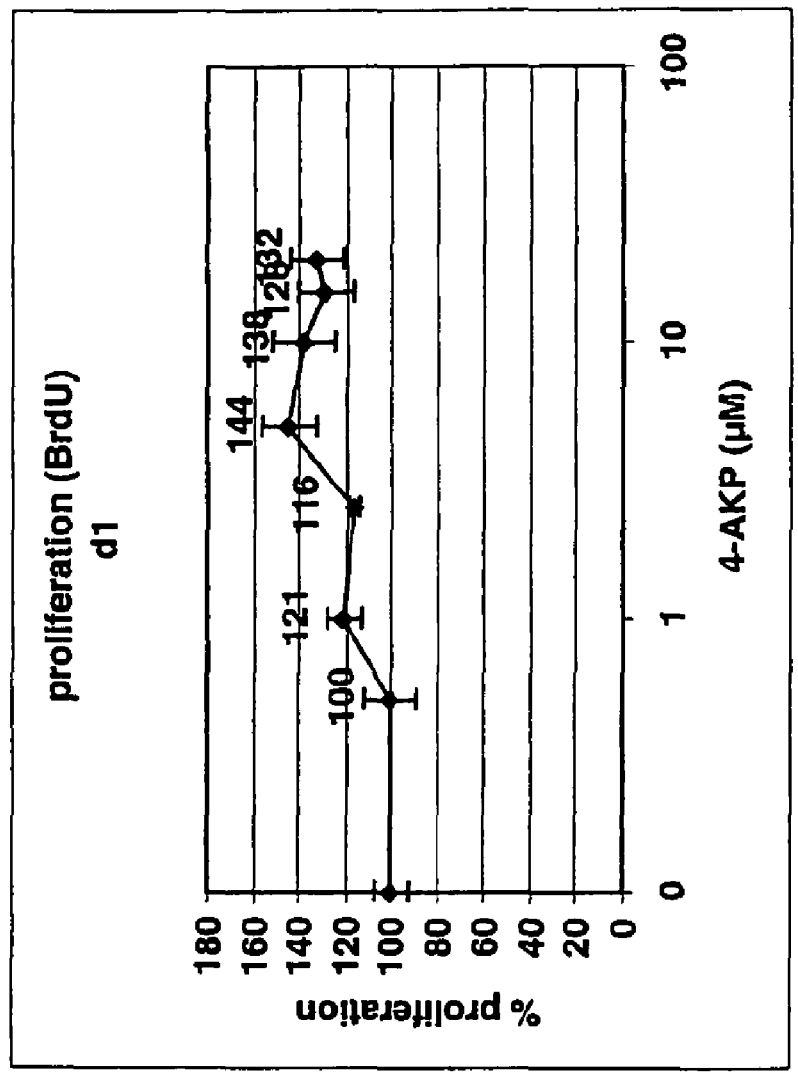
Figure 3:
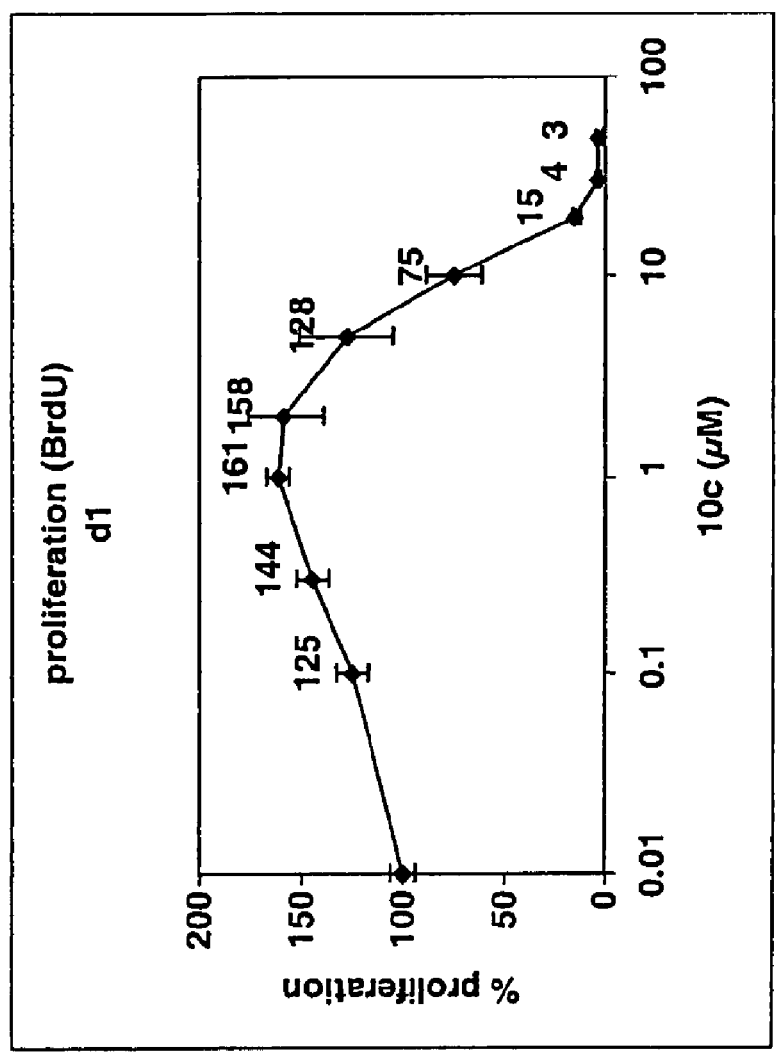

FIG. 3 shows the proliferation rate of INS-1E insulinoma cells treated with compound 10c relative to untreated controls. As explained in FIG. 1, the proliferation of Ins-1E cells was determined by monitoring DNA synthesis as an indirect parameter of cell proliferation. The compound 10c increases BrdU incorporation of cycling Ins-1E cells reaching a maximum of about 1.5 fold at 1 μM.

Figure 4:
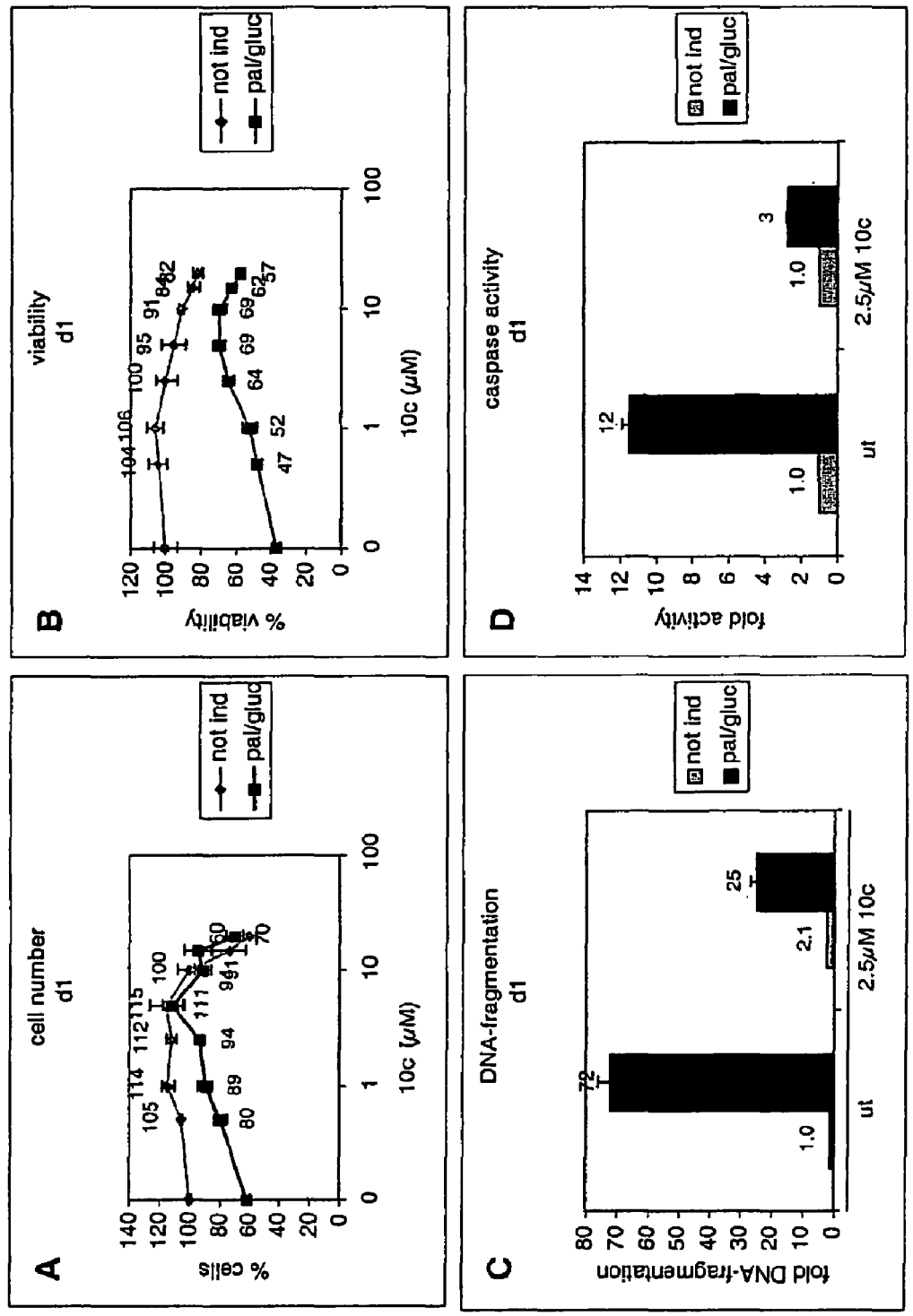

FIG. 4 shows the effect of 10c on glucolipotoxicity induced apoptosis (referred to as "pal/gluc"; black line and quarters or black bars in FIG. 4C and FIG. 4D) of INS-1E cells compared to control INS-1E cells (referred to as "not ind"; light grey line and quarters or light grey bars in FIG. 4C and FIG. 4D). Experiments were carried out as described under FIG. 2 and in the material and method section under Example 3. Compound 10c strongly antagonizes glucolipotoxicity induced apoptosis.

FIG. 4A shows the effects of 10c on cell growth.

FIG. 4B shows the effects of compound 10c on cell viability.

FIG. 4C shows that the amount of cytosolic DNA-fragments is reduced by 74% in the presence of 2.5 μM 10c.

FIG. 4D shows that caspase activity is reduced by 77% in the presence of 2.5 μM 10c.

Figure 5:
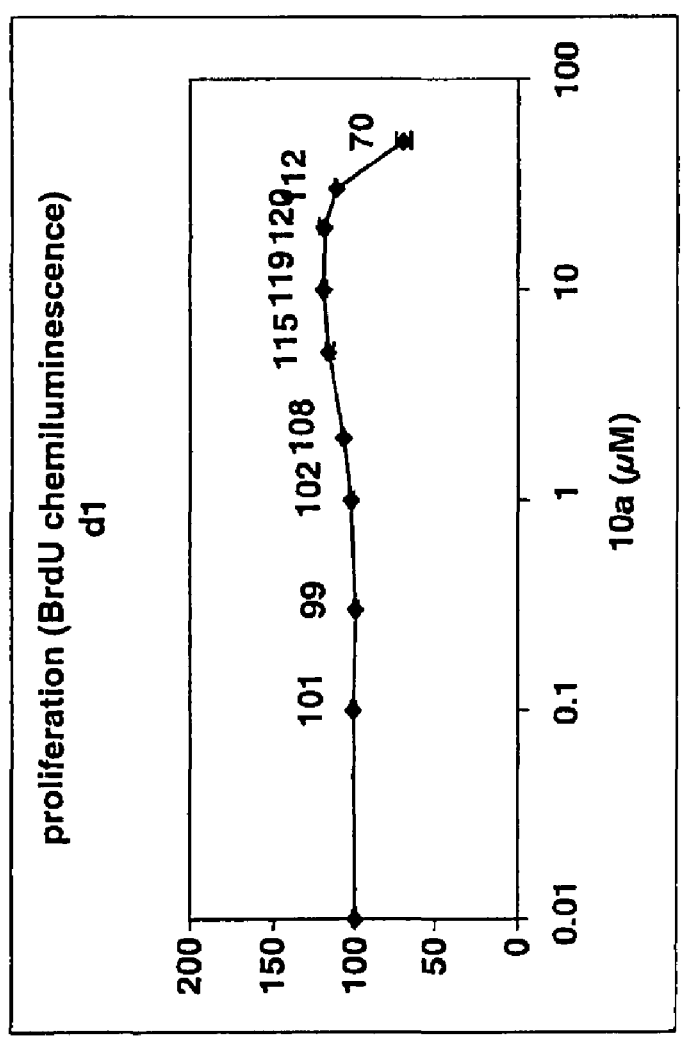

FIG. 5 shows the proliferation rate of INS-1E insulinoma cells treated with compound 10a relative to untreated controls. Compound 10a has a small effect on INS-1 proliferation and increases the BrdU incorporation of cycling Ins-1E cells at most of about 1.2 fold at about 10 μM.

Figure 6:
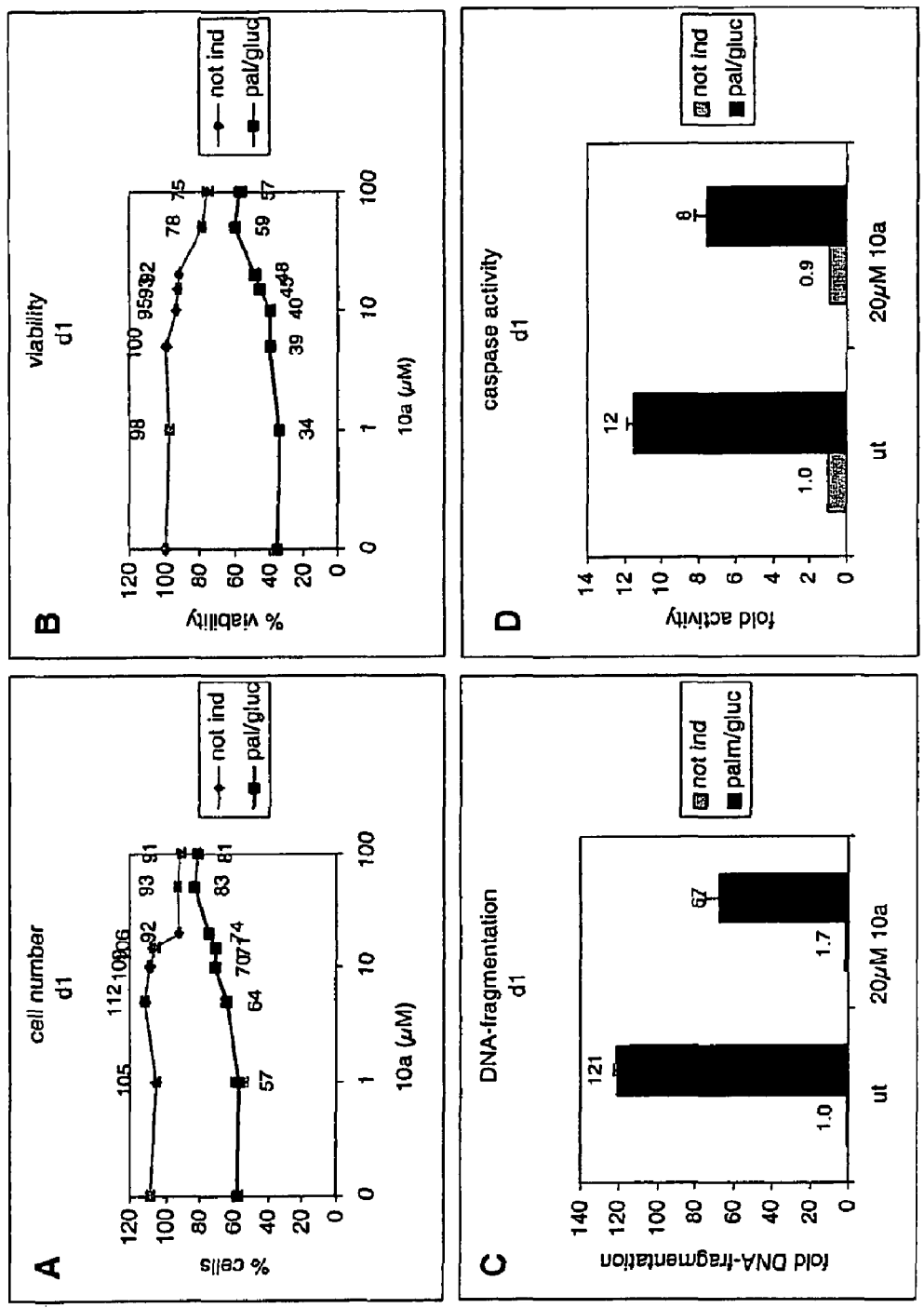

FIG. 6 shows the effect of 10a on glucolipotoxicity induced apoptosis (referred to as "pal/gluc"; black line and quarters or black bars in FIG. 6C and FIG. 6D) of INS-1E cells compared to control INS-1E cells (referred to as "not ind"; light grey line and quarters or light grey bars in FIG. 6C and FIG. 6D). Experiments were carried out as described under FIG. 2 and in the material and method section under Example 3. Compound 10a moderately prevents glucolipotoxicity induced apoptosis of INS-1E cells.

FIG. 6A shows the effects of 10a on cell growth.

FIG. 6B shows the effects of 10a on cell viability.

FIG. 6C shows that the amount of cytosolic DNA-fragments is reduced by 44% in the presence of 20 μM 10a.

FIG. 6D shows that caspase activity is reduced by 22% in the presence of 20 μM 10a.

Figure 7:
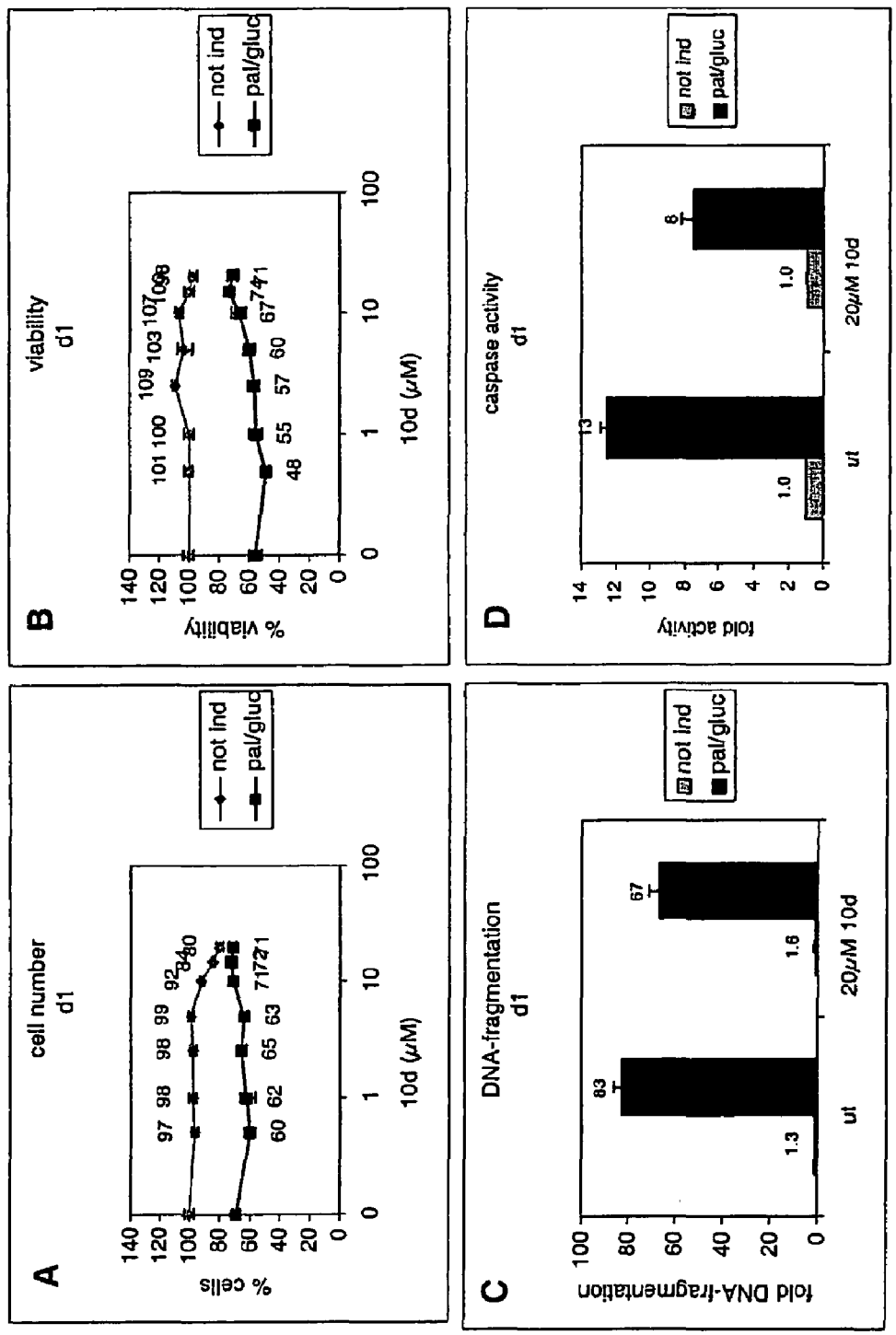

FIG. 7 shows the effect of compound 10d on glucolipotoxicity induced apoptosis (referred to as "pal/gluc"; black line and quarters or black bars in FIG. 7C and FIG. 7D) of INS-1E cells compared to control INS-1E cells (referred to as "not ind"; light grey line and quarters or light grey bars in FIG. 7C and FIG. 7D). Experiments were carried out as described under FIG. 2 and in the material and method section under Example 3. Compound 10d slightly effects glucolipotoxicity induced apoptosis of INS-1E cells.

FIG. 7A shows the effects of 10d on cell growth.

FIG. 7B shows the effects of 10d on cell viability.

FIG. 7C shows that the amount of cytosolic DNA-fragments is reduced by 23% in the presence of 20 µM 10d.

FIG. 7D shows that caspase activity is reduced by 27% in the presence of 20 µM 10d.

Figure 8:
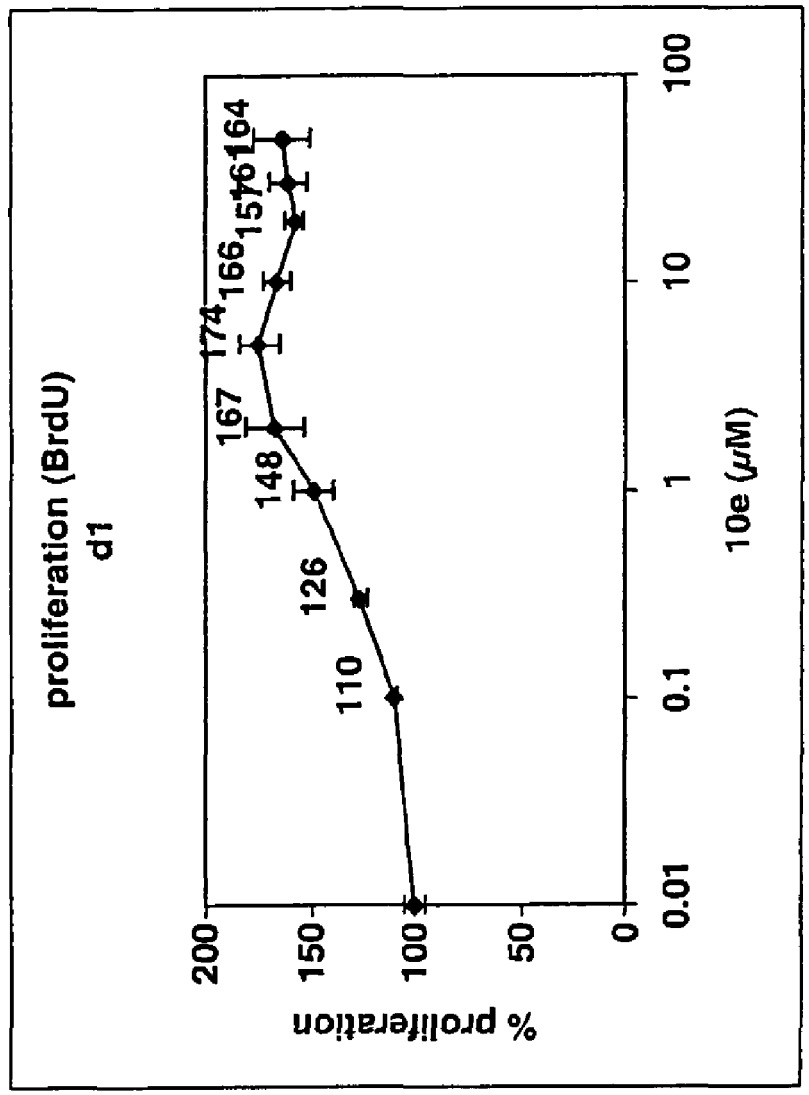

FIG. 8 is a graph showing the proliferation rate of INS-1E insulinoma cells treated with compound 10e relative to untreated controls. 10E increases the BrdU incorporation of cycling Ins-1E cells up to about 1.7 fold, reaching the maximum between 1 µM and 10 µM.

Figure 9:
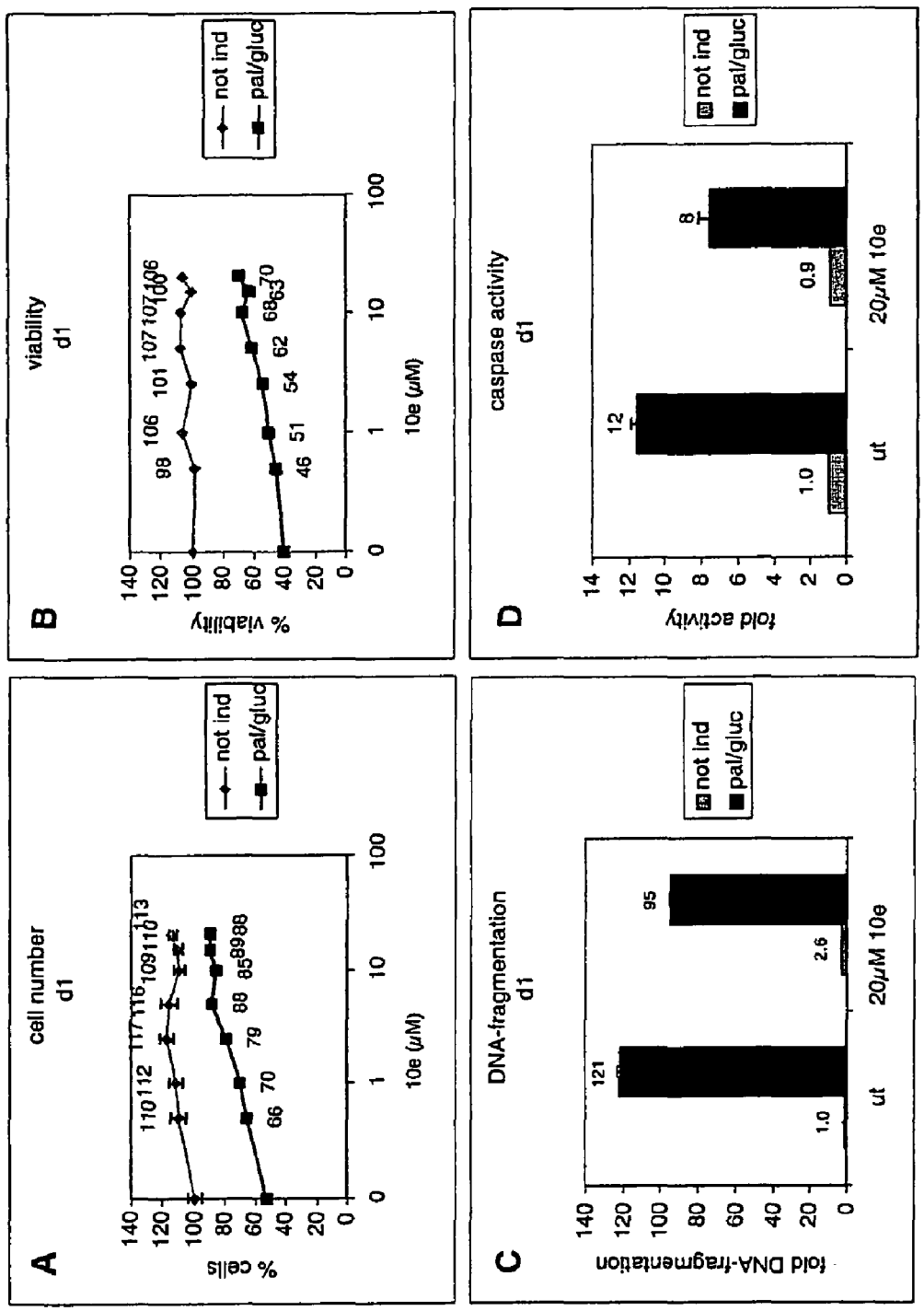

FIG. 9 shows the effect of compound 10e on glucolipotoxicity induced apoptosis (referred to as "pal/gluc"; black line and quarters or black bars in FIG. 9C and FIG. 9D) of INS-1E cells compared to control INS-1E cells (referred to as "not ind"; light grey line and quarters or light grey bars in FIG. 9C and FIG. 9D). Experiments were carried out as described under FIG. 2 and in the material and method section under Example 3. 10e slightly prevents glucolipotoxicity induced apoptosis.

FIG. 9A shows the effects of 10e on cell growth.

FIG. 9B shows the effects of 10e on cell viability.

FIG. 9C shows that the amount of cytosolic DNA-fragments is reduced by 23% in the presence of 20 µM 10e.

FIG. 9D shows that caspase activity is reduced by 16% in the presence of 20 µM 10e.

Figure 10:
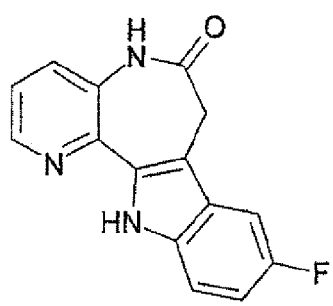
Figure 10:
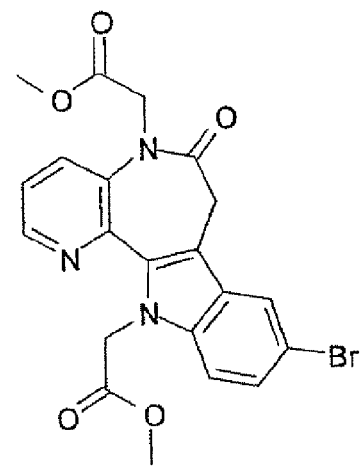
Figure 10:
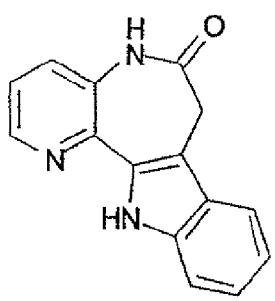
Figure 10:
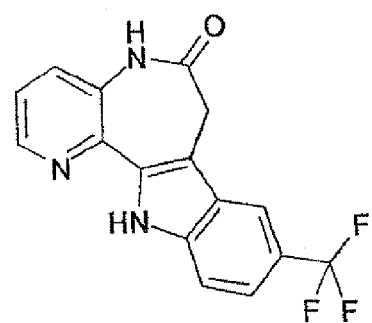
Figure 10:
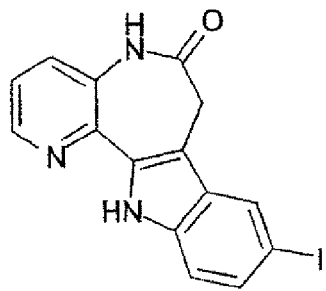

FIG. 10 shows structural formulae of compounds 10a-10i and 10k-10m.

Figure 11:
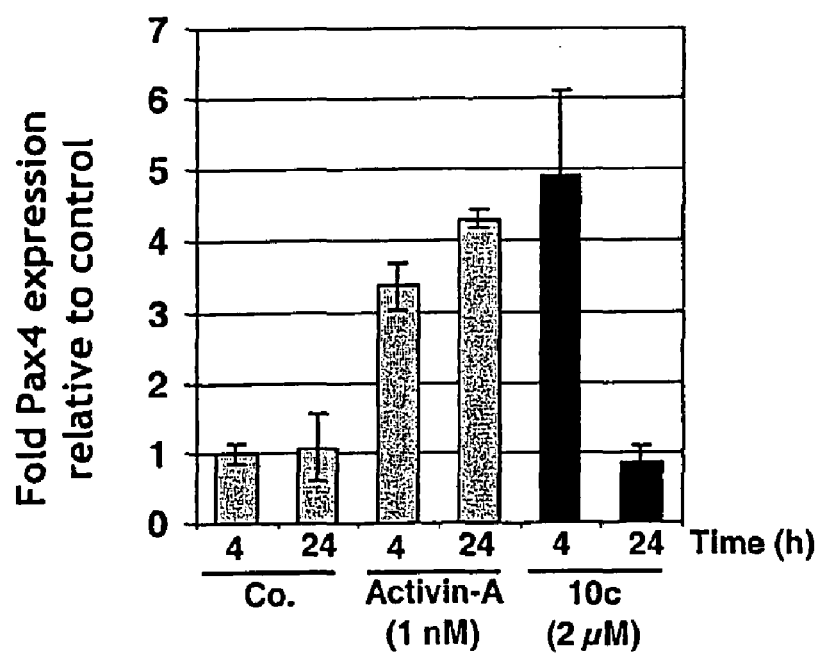

FIG. 11 illustrates a representative experiment in which the relative Pax4 levels were quantified using quantitative real time RT-PCR. Compound 10c (2 µM) has been found to transiently induce Pax4 gene transcription in INS-1E cells. Data are presented as relative levels to the basal Pax4 expression level in INS-1E cells only treated with the vehicle (Co.). Activin-A (1 nM) treated INS-1E cells serve as a positive control.

Figure 12:
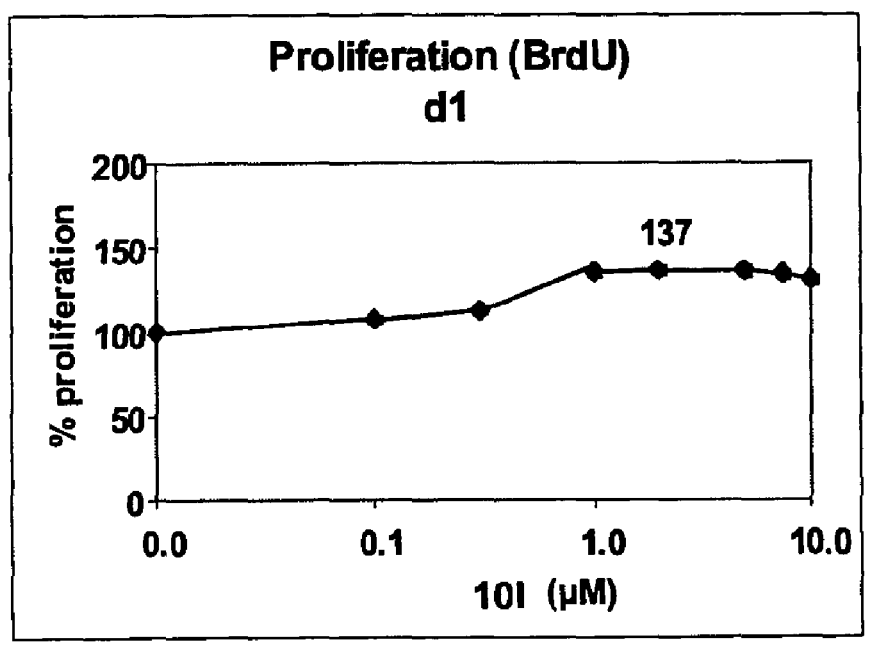

FIG. 12 is a graph showing the proliferation rate of INS-1E insulinoma cells treated with compound 10l relative to untreated controls. 10l increases the BrdU incorporation of cycling Ins-1E cells up to about 1.4 fold, reaching the maximum between 1 µM and 5 µM.

Figure 13:
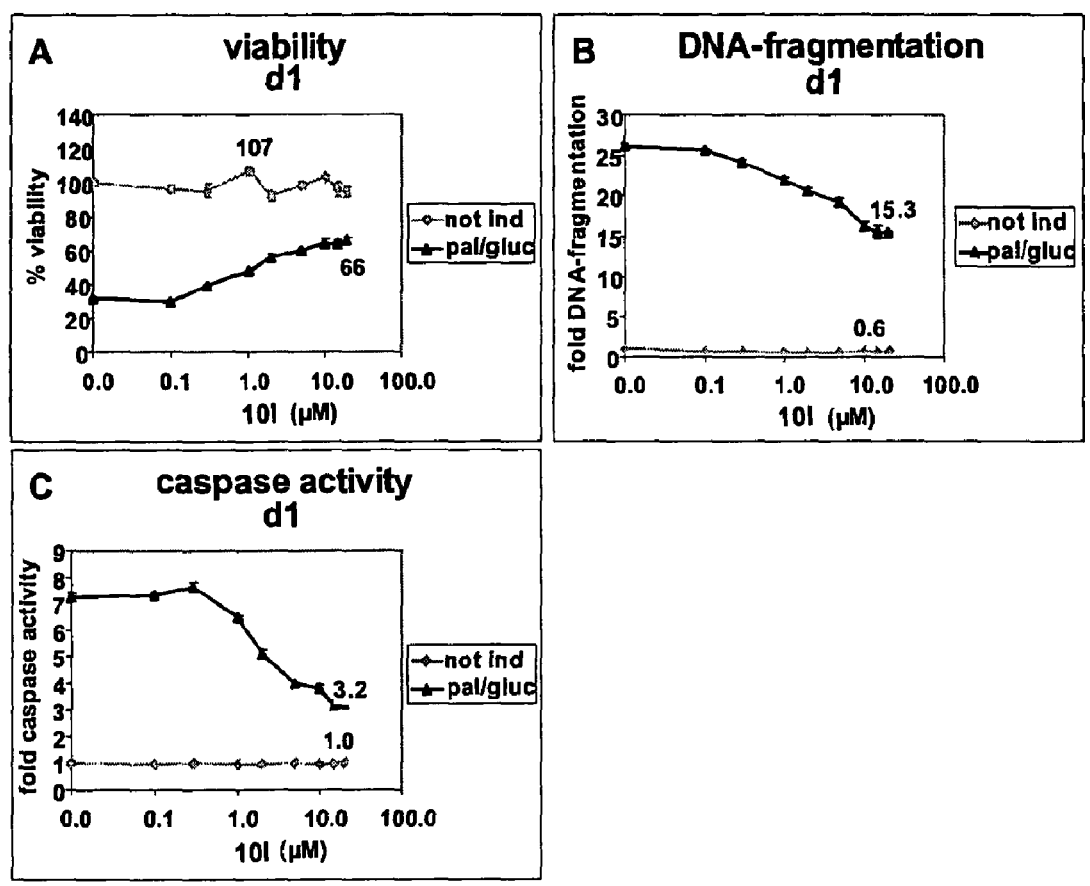

FIG. 13 shows the effect of compound 10l on glucolipotoxicity induced apoptosis (referred to as "pal/gluc"; black line and triangles) of INS-1E cells compared to control INS-1E cells (referred to as "not ind"; light grey line and diamond). Experiments were carried out as described under FIG. 2 and in the material and method section under Example 3. Compound 10l significantly effects glucolipotoxicity induced apoptosis of INS-1E cells.

FIG. 13A shows the effects of 10l on cell viability.

FIG. 13B shows the effects of 10l on apoptotic processes in INS-1E cell death monitored by the production of cytosolic DNA-fragments.

FIG. 13C shows the effects of 10l on apoptotic processes in INS-1E cell death monitored by the activity of caspases.

FIG. 14 shows that compound 10c and e are selective kinase inhibitors. The enzymatic activity of only a few kinases is strongly inhibited by the test compounds. Experiments were carried out by Upstate Ltd. according to the protocols described in KinaseProfiler™ Assay Protocols Fall 2004 by Ustate Cell Signaling solutions.

Figure 15:
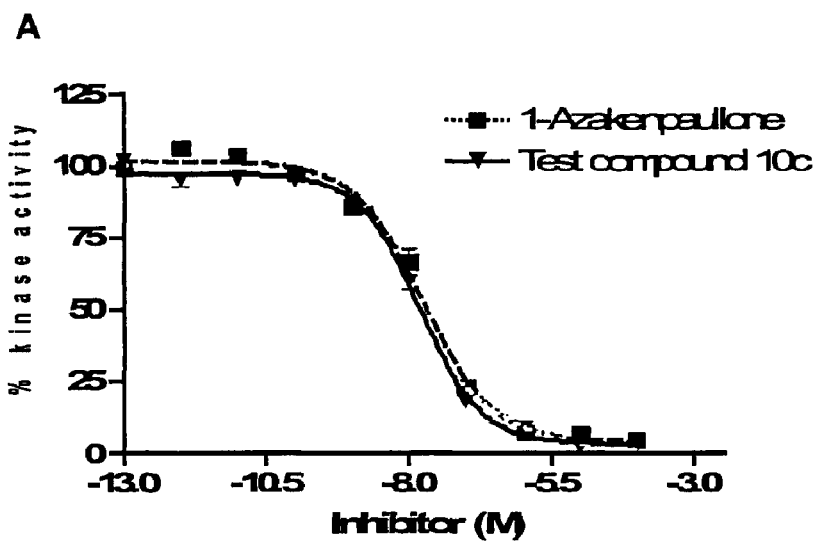
Figure 15:
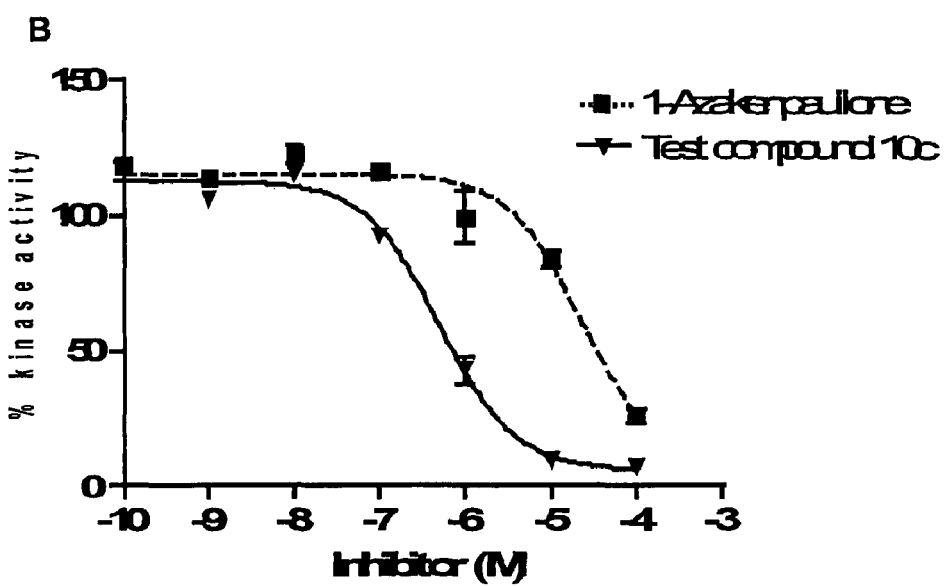

FIG. 15 shows that compound 10c is like 1-Azakenpaullone a potent inhibitor of human GSK3. Experiments were carried out by Upstate Ltd. according to the protocols described in KinaseProfiler™ Assay Protocols, IC50 Profiler Express™ (10-point curves in duplicate) Fall 2004 by Ustate Cell Signaling solutions.

Figure 16:
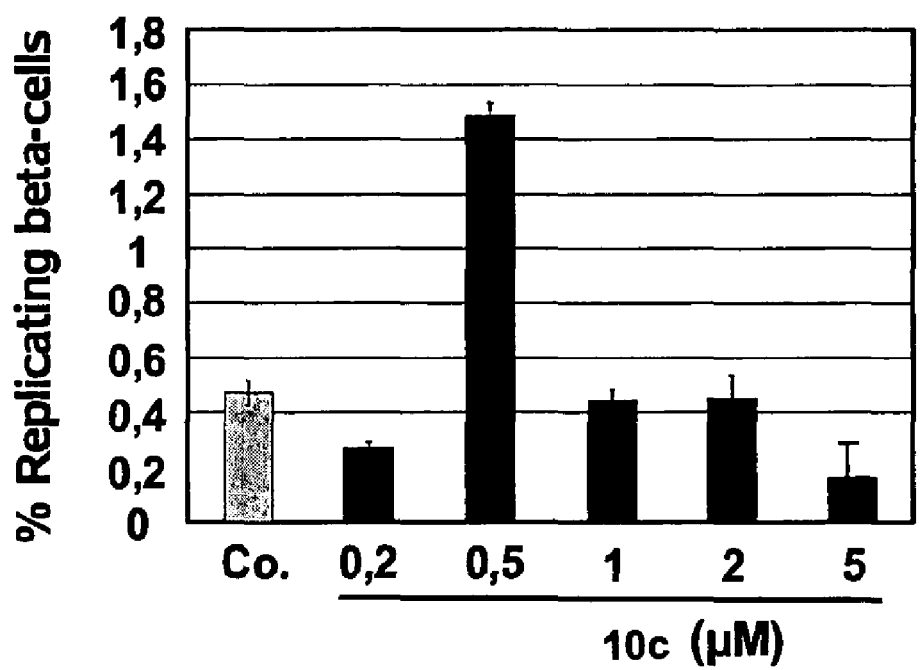

FIG. 16 illustrates that compound 10c stimulates the replication of primary rat beta cells in culture. Cells expressing the proliferation marker Ki67 as well as C-peptide were considered to be replicating beta cells. The percentage of replicating beta cells in islets not exposed to compound 10c (Co.) and islet treated for 72 hours with the indicated amounts of compound 10c was determined by immunofluorescence microscopy.

EXAMPLE 1

Synthesis of Azapaullones

The following instruments were used for synthetic procedures, determination of compound properties and recording spectra:

Microwave device: CEM Discover focussed microwave synthesis system running with ChemDriver Software; Melting points: Electrothermal IA 9100; IR spectra: ATI Mattson Genesis Series FT-IR spectrometer; NMR spectra: Bruker AM 400 or Bruker Avance DRX 400; Elemental analyses: Carlo Erba C—H—N—O Elemental Analyzer 1106 or Thermo Quest CE Instruments FlashEA 1112 Elemental Analyzer; Mass spectra: Finnigan-MAT 8430 or Finnigan-MAT 8400 MSS I or Finnigan-Mat 90 (EI-MS: Ionisation energy 70 eV); HPLC: Merck Hitachi L-2000 series; Merck Hitachi diode array detector L-2450; Column: Merck LiChroCART 125-4, LiChrospher 100 RP-18 (5 µm), flow rate: 1 mL/min., oven temperature: 25° C.; isocratic elution, detection wavelength 254 nm.

General Procedure A for the Synthesis of Phenyl Hydrazones

5H-Pyrido[3,2-b]azepine-6,9(7H,8H)-dione (1 mmol) and an appropriate substituted phenylhydrazine (1.5 mmol), [(or an appropriate substituted phenylhydrazine hydrochloride, (1.1 mmol) and sodium acetate (1.1 mmol), respectively] are suspended in glacial acetic acid (10 mL) and stirred for 30 minutes at 70° C. After cooling to room temperature, the mixture is poured into a 5% aqueous sodium acetate solution. The precipitate is filtered off with suction, washed successively with 5% aqueous sodium acetate solution and water and purified by recrystallization from ethanol.

General Procedure B

An appropriate phenyl hydrazone (1 mmol), obtained by General Procedure A, is refluxed in diphenyl ether (80 mL) under nitrogen for 2 hours. The mixture is allowed to cool to room temperature. Upon addition of n-hexane (100 mL) a precipitate forms, which is separated by filtration and washed with petrol ether. The material is purified by recrystallization from ethanol.

General Procedure C

An appropriate phenyl hydrazone (0.1 mmol), obtained by General Procedure A, is heated in water (1 mL) in a sealed microwave reaction vessel by means of a monomode microwave device (CEM Discover). The reaction is conducted under the following conditions:

| | |
|---|---|
| ramp time | 15 minutes |
| reaction time | 30 minutes |
| reaction temperature | 230° C. |

After cooling to room temperature, the precipitate is filtered off and washed successively with petrol ether and water.

9-Methoxy-7,12-dihydro-pyrido[3',2':2,3]azepino[4,5-b]indole-6(5H)-one (10a)

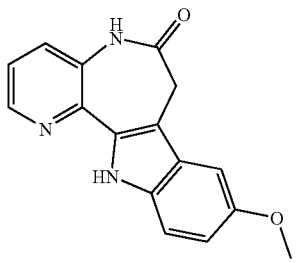

5H-Pyrido[3,2-b]azepine-6,9(7H,8H)-dione (484 mg; 2.74 mmol), (4-methoxyphenyl)hydrazine hydrochloride (527 mg, 3.02 mmol), and sodium acetate (242 mg; 3.02 mmol) were suspended in glacial acetic acid (30 mL) and stirred for 30 min. at 70° C. After cooling to room temperature, the mixture was poured into a 5% aqueous sodium acetate solution. The precipitate, consisting of the corresponding phenyl hydrazone, was filtered off with suction, washed successively with 5% aqueous sodium acetate solution and water and was then refluxed 4 h in 70 mL ethanol. After cooling, 206 mg (27%) of a brown powder precipitated, m.p. >330° C.; IR (KBr): 3269 cm$^{-1}$ (NH), 1669 cm$^{-1}$ (C=O); $^1$H-NMR (d$_6$-DMSO, 400 MHz): δ (ppm)=3.66 (s, 2H, azepine-CH$_2$), 3.81 (s, 3H, OCH$_3$), 6.84 (dd, 1H, 8.8/2.4 Hz, arom. H), 7.21 (d, 1H, 2.3 Hz, arom. H), 7.35-7.40 (m, 2H, arom. H), 7.60 (dd, 1H, 8.2/1.4 Hz, arom. H), 8.46 (dd, 1H, 4.5/1.4 Hz, arom. H), 10.20 (s, 1H, NH), 11.54 (s, 1H, NH); $^{13}$C-NMR (DMSO-d$_6$, 100.6 MHz): δ (ppm)=55.4 (OCH$_3$), 31.8 (azepine-CH$_2$), 99.6, 112.7, 113.6, 122.3, 129.3, 144.2 (tert. arom. C-atoms), 108.7, 126.6, 131.9, 132.7, 133.0, 140.6, 153.5 (quat. arom. C-atoms), 171.2 (C=O). purity: 99.8% (HPLC, t$_s$=3.57 min, acetonitrile/water: 25/75); EI/HRMS for C$_{16}$H$_{13}$N$_3$O$_2$ (279.30) calculated: 279.10077. found: 279.10010.

4-[2-(6-oxo-5,6,7,8-tetrahydro-9H-pyrido[3,2-b]azepino-9-ylidene]hydrazino]benzoic acid

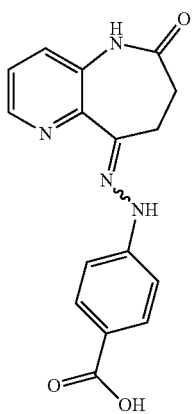

Prepared according to General Procedure A from 176 mg (1 mmol) 5H-pyrido[3,2-b]azepine-6,9(7H,8H)-dione, and 228 mg (1.5 mmol) 4-hydrazinobenzoic acid. Recrystallization afforded 110 mg (35%) of a yellow powder, m.p.: 284° C. (dec.). IR (KBr): 3430 cm$^{-1}$ (NH), 3267 cm$^{-1}$ (NH), 1678 cm$^{-1}$ (C=O), $^1$H-NMR (d$_6$-DMSO, 400 MHz): δ (ppm)= 2.56-2.59 (m, AA'XX', 2H, azepine-CH$_2$), 3.06-3.10 (m, AA'XX', 2H, azepin-CH$_2$), 7.23 (d, 2H, 8.8 Hz, arom. H), 7.36-7.42 (m, 2H, arom. H), 7.81 (d, 2H, 8.8 Hz, arom. H), 8.42 (dd, 1H, 4.3/1.8 Hz, arom. H), 9.76 (s, 1H, NH), 9.79 (s, 1H, NH), 12.31 (bs, 1H, COOH), $^{13}$C-NMR (DMSO-d$_6$, 100.6 MHz): δ (ppm)=29.9, 30.5 (azepine-CH$_2$), 112.3, 123.6, 129.4, 130.8, 145.4 (tert. arom. C-atoms), 121.3, 134.4, 144.3, 147.8, 149.1 (quat. arom. C-atoms), 167.2, 172.8 (C=O).

6-Oxo-5,6,7,12-tetrahydropyrido[3',2':2,3]azepino[4,5-b]indole-9-carboxylic acid (10 b)

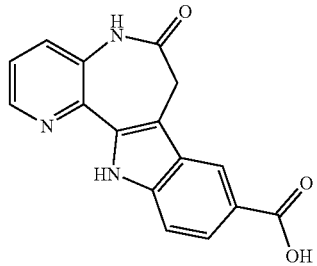

Prepared according to General Procedure B from 101 mg (0.33 mmol) 4-[2-(6-oxo-5,6,7,8-tetrahydro-9H-pyrido[3,2-b]azepino-9-ylidene]hydrazino]benzoic acid in 30 mL diphenyl ether. Recrystallization from ethanol afforded 28 mg (29%) black powder; m.p. >330° C. IR (KBr): 3398 cm$^{-1}$ (NH), 3193 cm$^{-1}$/3066 cm$^{-1}$ (CH-arom.), 2977 cm$^{-1}$/2923 cm$^{-1}$ (CH-aliph.), 1675 cm$^{-1}$ (C=O); $^1$H-NMR (DMSO-d$_6$, 400 MHz): δ (ppm)=3.71 (s, 2H, azepine-CH$_2$), 7.44 (dd, 1H, 8.2/4.5 Hz, arom. H), 7.53 (dd, 1H, 9.0/0.4 Hz, arom H.), 7.65 (dd, 1H, 8.3/1.4 Hz, arom. H), 7.83 (dd, 1H, 8.6/1.6 Hz, arom. H), 8.37 (s, 1H, arom. H), 8.50 (dd, 1H, 4.5/1.4 Hz, arom. H), 10.27 (s, 1H, NH), 12.10 (s, 1H, NH), 12.51 (bs, 1H, COOH), $^{13}$C-NMR (DMSO-d$_6$, 100,6 MHz): δ (ppm)=31.7 (azepine-CH$_2$), 111.7, 121.0, 122.9, 123.9, 129.4, 144.3 (tert. arom. C-atoms), 109.9, 121.8, 125.8, 132.4, 134.1, 139.8, 139.9 (quat. arom. C-atoms), 168.1, 170.7 (C=O). EI/HRMS for C$_{16}$H$_{11}$N$_3$O$_3$ (293.28) calculated: 293.08005. found: 293.07956. Purity: 99.2% (HPLC; t$_s$=3.99 min, acetonitrile/water:15/85).

4-[2-(6-Oxo-5,6,7,8-tetrahydro-9H-pyrido[3,2-b]azepin-9-ylidene)hydrazino]benzonitrile

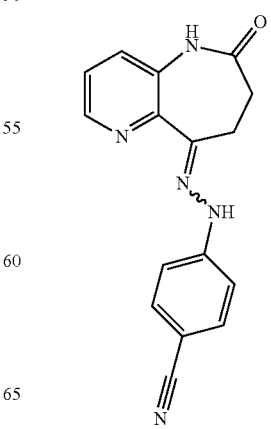

Prepared according to General Procedure A from 260 mg (1.14 mmol) 5H-pyrido[3,2-b]azepine-6,9(7H,8H)-dione, 275 mg (1.62 mmol) 4-hydrazinobenzonitrile, and 130 mg (1.62 mmol) sodium acetate. Recrystallization from ethanol afforded 317 mg (72%) yellow crystals, m.p. 273° C. (dec.). IR (KBr): 3433 cm$^{-1}$/3278 cm$^{-1}$, 3185 cm$^{-1}$/3120 cm$^{-1}$/3063 cm$^{-1}$ (CH-arom.), 2957 cm$^{-1}$/2888 cm$^{-1}$, 2218 cm$^{-1}$ (C≡N), 1673 cm$^{-1}$ (C=O); $^1$H-NMR (DMSO-d$_6$, 400 MHz): δ (ppm)=2.56-2.60 and 3.06-3.10 (m, AA'XX'-system, 4H, azepine-CH$_2$), 7.27-7.31 (m, part of AA'XX'-system, 2H, arom. H), 7.37-7.43 (m, 2H, arom. H), 7.61-7.64 (m, part of AA'XX'-system, 2H, arom. H), 8.42 (dd, 1H, 4.2/1.9 Hz, arom. H), 9.80 (s, 1H, NH), 9.92 (s, 1H, NH).

6-Oxo-5,6,7,12-tetrahydropyrido[3',2':2,3]azepino[4,5-b]indole-9-carbonitrile (10c)

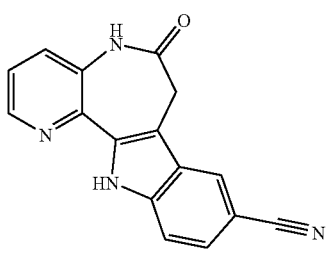

Preparation of 6-oxo-5,6,7,12-tetrahydropyrido[3',2':2,3]azepino[4,5-b]indole-9-carbonitrile (10c) is either accomplished by employing General Procedure B or C.

For the preparation according to General Procedure B 4-[2-(6-oxo-5,6,7,8-tetrahydro-9H-pyrido[3,2-b]azepino-9-ylidene]hydrazino]benzonitrile (260 mg; 0.89 mmol) were heated in 70 mL diphenyl ether. Recrystallization from ethanol afforded 45 mg (18%) brown powder, m.p. >330° C.; IR (KBr): 3382/3187 cm$^{-1}$ (NH), 3057 cm$^{-1}$ (CH-arom.), 2971 cm$^{-1}$ (CH-aliph.), 2220 cm$^{-1}$ (C≡N), 1672 cm$^{-1}$ (C=O); $^1$H-NMR (d$_6$-DMSO, 400 MHz): δ (ppm)=3.76 (s, 2H, azepine-CH$_2$), 7.46 (dd, 1H, 8.2/4.5 Hz, arom. H), 7.53 (dd, 1H, 8.5/1.5 Hz, arom. H), 7.62 (dd, 1H, 8.5/0.5 Hz, arom. H), 7.65 (dd, 1H, 8.2/1.4 Hz, arom. H), 8.38 (s, 1H, arom. H), 8.51 (dd, 1H, 4.5/1.4 Hz, arom. H), 10.34 (s, 1H, NH), 12.30 (s, 1H, NH), $^{13}$C-NMR (DMSO-d$_6$, 100.6 MHz): δ (ppm)=31.5 (azepine-CH$_2$), 113.0, 123.3, 124.6, 125.3, 129.5, 144.4 (tert. arom. C-atoms), 101.2, 109.5, 120.5, 126.2, 132.6, 134.9, 139.0, 139.4 (quat. arom. C-atoms) 171.8 (C=O); EI/HRMS for C$_{16}$H$_{10}$N$_4$O (274.28) calculated: 274.08545. found: 274.08499. purity: 98.8% (HPLC, t$_s$=3.49 min, acetonitrile/water:25/75).

The preparation according to General Procedure C from 27 mg (0.10 mmol) 4-[2-(6-oxo-5,6,7,8-tetrahydro-9H-pyrido[3,2-b]azepino-9-ylidene]hydrazino]benzonitrile in 1 mL water yielded 10 mg of a brown powder (36%) which displayed spectroscopic data ($^1$H-NMR) in agreement with the data of the material prepared by General Procedure B.

9-Hydroxy-7,12-dihydropyrido[3',2':2,3]azepino[4,5-b]indole-6(5H)-one (10d)

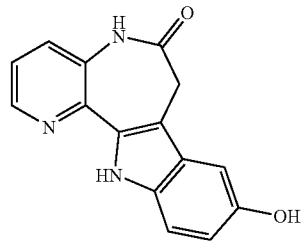

9-Methoxy-7,12-dihydropyrido[3',2':2,3]azepino[4,5-b]indole-6(5H)-one (10a, 71 mg, 0.25 mmol) and boron tribromide (246 mg, 1.0 mmol) were stirred in 10 mL dry dichloromethane at room temperature for 2 hours. Subsequently, 10 mL water were added and the mixture was stirred for one more hour. The precipitate was filtered off and recrystallized from ethanol, yielding 34 mg (50%) of a yellow powder, m.p.: >300° C.; IR (KBr): 3388/3189 cm$^{-1}$ (NH), 3064 cm$^{-1}$ (CH-arom.), 2981/2923 cm$^{-1}$ (CH-aliph.), 1671 cm$^{-1}$ (C=O); $^1$H-NMR (d$_6$-DMSO, 400 MHz): δ (ppm)=3.53 (s, 2H, azepine-CH$_2$), 6.73 (dd, 1H, 8.7/2.2 Hz, arom. H), 6.93 (d, 1H, 2.0 Hz, arom. H), 7.27 (d, 1H, 8.7 Hz, arom. H), 7.37 (dd, 1H, 8.1/4.5 Hz, arom. H), 7.59 (dd, 1H, 8.2/1.2 Hz, arom. H), 8.45 (dd, 1H, 4.4/1.2 Hz, arom. H) 8.80 (br s, 1H, OH), 10.16 (s, 1H, NH), 11.37 (s, 1H, NH), $^{13}$C-NMR (DMSO-d$_6$, 100.6 MHz): δ (ppm)=32.0 (azepine-CH$_2$), 101.7, 112.5, 114.1, 122.5, 130.2, 143.3 (tert. arom. C-atoms), 108.9, 126.9, 131.7, 132.2, 132.4, 139.9, 151.0 (quat. arom. C-atoms), 171.1 (C=O); EI/HRMS for C$_{15}$H$_{11}$N$_3$O$_2$ (265.27): calculated: 265.08511. found: 265.08405. purity: 95% by $^1$H-NMR, 97.5% by HPLC (t$_s$=3.88 min, acetonitrile/water: 10/90).

7,8-dihydro-5H-pyrido[3,2-b]azepine-6,9-dione 9-[(4-chlorophenyl)hydrazone]

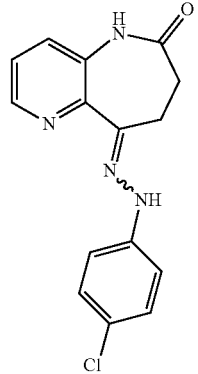

Prepared according to General Procedure A from 160 mg (0.9 mmol) 5H-pyrido[3,2-b]azepine-6,9(7H,8H)-dione, 178 mg (1.0 mmol) (4-chlorophenyl)hydrazine hydrochloride, and 82 mg (1.0 mmol) sodium acetate. Recrystallization from ethanol afforded 222 mg (82%) yellow crystals, m.p. 220° C.;

IR (KBr): 3434 cm$^{-1}$/3286 cm$^{-1}$ (NH), 3188 cm$^{-1}$/3127 cm$^{-1}$ (CH-arom.), 2956 cm$^{-1}$/2889 cm$^{-1}$ (CH-aliph.), 1677 cm$^{-1}$ (C=O); $^1$H-NMR (DMSO-d$_6$, 400 MHz): δ (ppm)=2.55-2.58 (m, 2H, AA'XX'-system, azepine-CH$_2$), 3.01-3.05 (m, 2H, AA'XX'-system, azepine-CH$_2$), 7.17-7.26 (m, 4H, AA'BB'-system, arom. H), 7.35 (dd, 1H, 8.0/4.4 Hz, arom. H), 7.39 (dd, 1H, 8.1/1.7 Hz, arom. H), 8.40 (dd, 1H, 4.4/1.7 Hz, arom. H), 9.46 (s, 1H, NH), 9.76 (s, 1H, NH).

9-Chloro-7,12-dihydropyrido[3',2':2,3]azepino[4,5-b]indole-6(5H)-one (10e)

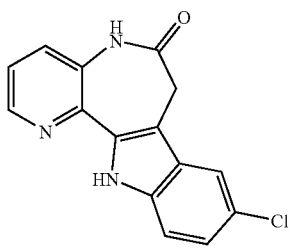

Prepared according to General Procedure B from 200 mg (0.66 mmol) 7,8-dihydro-5H-pyrido[3,2-b]azepine-6,9-dione 9-[(4-chlorophenyl)hydrazone] in 55 mL diphenyl ether. Recrystallization from ethanol afforded 49 mg (26%) of a grey powder; m.p. >330° C. IR (KBr): 3429/3191 cm$^{-1}$ (NH), 3061 cm$^{-1}$ (CH-arom.), 2975/2916 cm$^{-1}$ (CH-aliph.), 1679 cm$^{-1}$ (C=O); $^1$H-NMR (d$_6$-DMSO, 400 MHz): δ (ppm)= 3.68 (s, 2H, azepine-CH$_2$), 7.19 (dd, 1H, 8.6/2.0 Hz, arom. H), 7.43 (dd, 1H, 8.2/4.5 Hz, arom. H), 7.47 (d, 1H, 8.6 Hz, arom. H), 7.63 (dd, 1H, 8.2/1.4 Hz, arom. H), 7.82 (d, 1H, 2.0 Hz, arom. H), 8.49 (dd, 1H, 4.5/1.4 Hz, arom. H), 10.24 (s, 1H, NH), 11.91 (s, 1H, NH), $^{13}$C-NMR (DMSO-d$_6$, 100.6 MHz): δ (ppm)=31.6 (azepine-CH$_2$), 113.4, 117.8, 122.8, 122.9, 129.4, 144.3 (tert. arom. C-atoms), 108.5, 123.8, 127.3, 132.3, 134.1, 135.8, 139.9 (quat. arom. C-atoms), 170.9 (C=O); EI/HRMS for C$_{15}$H$_{10}$ClN$_3$O (283.72) calculated: 283.05124, found: 283.05077. purity: 99.5% (HPLC, t$_s$=3.17 min, acetonitrile/water:40/60).

7,8-Dihydro-5H-pyrido[3,2-b]azepine-6,9-dione 9-[(3,5-dichlorophenyl)hydrazone]

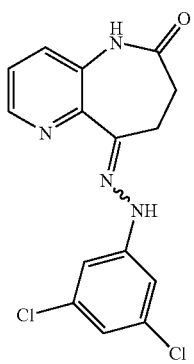

Prepared according to general procedure A from 338.5 mg (1.92 mmol) 5H-pyrido[3,2-b]azepine-6,9(7H,8H)-dione, 452 mg (2.11 mmol) (3,5-dichlorophenyl)hydrazine hydrochloride, and 169 mg (2.11 mmol) sodium acetate. Recrystallization from ethanol afforded a beige powder. Yield: 213 mg (33%); m.p. 270° C. (dec.); IR (KBr): 3281 cm$^{-1}$ (NH), 3067/3029 cm$^{-1}$ (CH-arom.), 2892 cm$^{-1}$ (CH-aliph.), 1671 cm$^{-1}$ (C=O); $^1$H-NMR (DMSO-d$_6$, 400 MHz): δ (ppm)= 2.57-2.60 (m, 2H, azepine-CH$_2$, part of AA'XX'-system), 3.02-3.05 (m, 2H, azepine-CH$_2$, part of AA'XX'-system), 6.91-6.92 (m, 1H, arom. H), 7.16 (d, 2H, 1.9 Hz, arom. H), 7.37-7.44 (m, 2H, arom. H), 8.44 (dd, 1H, 4.2/1.8 Hz, arom. H), 9.72 (s, 1H, NH), 9.81 (s, 1H, NH); C$_{15}$H$_{12}$Cl$_2$N$_4$O (335.20).

8,10-Dichloro-7,12-dihydropyrido[3',2':2,3]azepino[4,5-b]indol-6(5H)-one (10f)

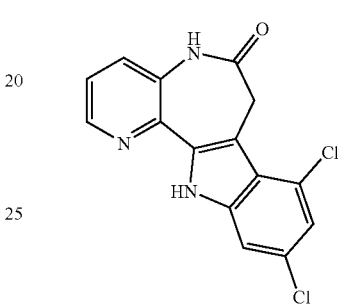

Prepared according to general procedure B from 159 mg (0.47 mmol) 7,8-dihydro-5H-pyrido[3,2-b]azepine-6,9-dione 9-[(3,5-dichlorophenyl)hydrazone] in 45 ml diphenyl ether. Recrystallization from ethanol afforded fine grey needles. Yield: 60 mg (40%); m.p. >330° C.; IR (KBr): 3186 cm$^{-1}$ (NH), 3083 cm$^{-1}$ (CH-arom.), 2971 cm$^{-1}$ (CH-aliph.), 1666 cm$^{-1}$ (C=O); $^1$H-NMR (DMSO-d$_6$, 400 MHz): δ (ppm)=3.96 (s, 2H, azepine-CH$_2$), 7.19 (d, 1H, 1.8 Hz, arom. H), 7.46-7.50 (m, 2H, arom. H), 7.64 (dd, 1H, 8.2/1.4 Hz, arom. H), 8.52 (dd, 1H, 4.5/1.4 Hz, arom. H), 10.35 (s, 1H, NH), 12.78 (s, 1H, NH); $^{13}$C-NMR (DMSO-d$_6$, 100.6 MHz): δ (ppm)=31.9 (azepine-CH$_2$), 110.9, 120.1, 123.4, 129.5, 144.5 (tert. arom. C), 108.1, 121.3, 125.3, 126.8, 132.7, 135.4, 138.6, 139.3 (quat. arom. C), 170.8 (C=O); EI/HRMS calculated for C$_{15}$H$_9$Cl$_2$N$_3$O (318.16): 317.0122, found: 317.0113. purity (HPLC): 99.1% (t$_s$=3.69 min, acetonitrile/water 40:60).

9-Methyl-7,12-dihydropyrido[3',2':2,3]azepino[4,5-b]indol-6(5H)-one (10g)

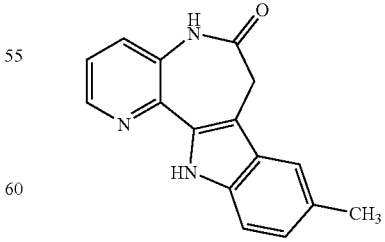

The precursor of the title compound, the corresponding phenyl hydrazone, was prepared according to general procedure A from 176 mg (1.0 mmol) 5H-pyrido[3,2-b]azepine-6,9(7H,8H)-dione and 174 mg (1.1 mmol) (4-methylphenyl)

hydrazine hydrochloride, and 90 mg (1.1 mmol) sodium acetate. The precipitate, consisting of the raw phenyl hydrazone, was filtered off with suction, washed successively with 5% aqueous sodium acetate solution and water and was then refluxed 6 h in 70 mL ethanol. After cooling, 64 mg (51%) of a white solid precipitated; m.p. >330° C.; IR: 3188 cm$^{-1}$ (NH), 3057 cm$^{-1}$ (CH-arom.), 2973/2912 cm$^{-1}$ (CH-aliph.), 1673 cm$^{-1}$ (C=O); $^1$H-NMR (d$_6$-DMSO, 400 MHz): δ (ppm)=2.41 (s, 3H, CH$_3$), 3.61 (s, 2H, azepine-CH$_2$), 7.02 (dd, 1H, 8.4/1.3 Hz, arom H.), 7.35-7.40 (m, 2H, arom. H), 7.47 (d, 1H, 0.5 Hz, arom. H), 7.60 (dd, 1H, 8.2/1.4 Hz, arom. H), 8.46 (dd, 1H, 4.5/1.4 Hz, arom. H), 10.18 (s, 1H, NH), 11.55 (s, 1H, NH); $^{13}$C-NMR (DMSO-d$_6$, 100.6 MHz): δ (ppm)=21.1 (CH$_3$), 31.9 (azepine-CH$_2$), 111.6, 117.8, 122.3, 124.6, 129.3, 144.2 (tert. arom. C), 108.4, 126.5, 127.6, 131.9, 132.5, 135.9, 140.6 (quat. arom. C) 171.0 (C=O); C$_{16}$H$_{13}$N$_3$O (263.30); purity (HPLC): 98.0% (t$_s$=3.91 min, acetonitrile/water 30:70).

7,8-Dihydro-5H-pyrido[3,2-b]azepine-6,9-dione 9-[(4-fluorophenyl)hydrazone]

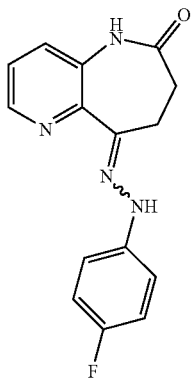

183 mg (1.04 mmol) 5H-Pyrido[3,2-b]azepine-6,9(7H,8H)-dione and 186 mg (1.14 mmol) (4-fluorophenyl)hydrazine hydrochloride, and 90 mg (1.1 mmol) sodium acetate were suspended in glacial acetic acid (11 ml) and stirred for 1 hour at 70° C. After cooling to room temperature, the mixture was poured into a 5% aqueous sodium acetate solution. The mixture was extracted with 4×20 ml ethyl acetate. The combined organic layers were dried over sodium sulfate, and evaporated to dryness. Recrystallization from ethanol afforded a yellow solid. Yield: 170 mg (58%);m.p. 232-233° C.; IR (KBr): 3286 cm$^{-1}$ (NH), 3119/3061 cm$^{-1}$ (CH-arom.) 2956/2888 cm$^{-1}$ (CH-aliph.), 1674 cm$^{-1}$ (C=O); $^1$H-NMR (DMSO-d$_6$, 400 MHz): δ (ppm)=2.54-2.58 (m, 2H, part of AA'XX'-system, azepine-CH$_2$), 3.01-3.04 (m, 2H, part of AA'XX'-system, azepine-CH$_2$), 7.03-7.07 (m, 2H, arom. H), 7.16-7.20 (m, 2H, arom. H), 7.33-7.40 (m, 2H, arom. H), 8.40 (dd, 1H, 4.4/1.6 Hz, arom. H), 9.35 (s, 1H, NH), 9.77 (s, 1H, NH); C$_{15}$H$_{13}$FN$_4$O (284.30).

9-Fluoro-7,12-dihydropyrido[3',2':2,3]azepino[4,5-b]indol-6(5H)-one (10h)

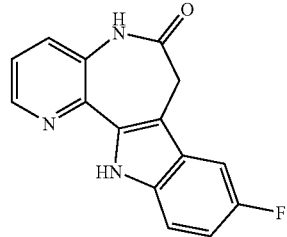

Preparation of 9-fluoro-7,12-dihydropyrido[3',2':2,3]azepino[4,5-b]indol-6(5H)-one is either accomplished by employing general procedure B or C. Preparation according to general procedure B from 123 mg (0.44 mmol) 7,8-dihydro-5H-pyrido[3,2-b]azepine-6,9-dione 9-[(4-fluorophenyl)hydrazone] in 45 ml diphenyl ether. Recrystallization from ethanol afforded a brown powder. Yield: 20 mg (17%).

Preparation according to general procedure C from 28 mg (0.10 mmol) 7,8-dihydro-5H-pyrido[3,2-b]azepine-6,9-dione 9-[(4-fluorophenyl)hydrazone] in 1 ml water yielded 14 mg of a brown powder (51%);m.p. >330° C.; IR (KBr): 3194 cm$^{-1}$ (NH), 3064 cm$^{-1}$ (CH-arom.), 2976/2917 cm$^{-1}$ (CH-aliph.), 1680 cm$^{-1}$ (C=O); $^1$H-NMR (DMSO-d$_6$, 400 MHz): δ (ppm)=3.66 (s, 2H, azepine-CH$_2$), 7.04 (ddd, 1H, 9.3/9.1/2.5 Hz, arom.H), 7.40-7.46 (m, 2H, arom. H), 7.54 (dd, 1H, 9.9/2.5 Hz, arom. H), 7.62 (dd, 1H, 8.2/1.4 Hz), 8.48 (dd, 1H, 4.5/1.4 Hz, arom. H), 10.23 (s, 1H, NH), 11.79 (s, 1H, NH); $^{13}$C-NMR (DMSO-d$_6$, 100.6 MHz): δ (ppm)=31.8 (azepine-CH$_2$), 103.2 (d, $^2$J$_{C,F}$=23 Hz), 111.1 (d, $^2$J$_{C,F}$=27 Hz), 112.9 (d, $^3$J$_{C,F}$=9 Hz), 122.8, 129.4, 144.3 (tert. arom. C), 108.9 (d, $^4$J$_{C,F}$=5 Hz), 126.5 (d, $^3$J$_{C,F}$=10 Hz), 132.2, 134.1, 134.3, 140.1, 157.0 (d, $^1$J$_{C,F}$=232 Hz) (quat. arom. C), 171.0 (C=O); C$_{15}$H$_{10}$FN$_3$O (267.26); purity (HPLC): 98.2% (t$_s$=3.00 min, acetonitrile/water 30:70).

Methyl 2-{9-bromo-12-[2-(methoxy-2-oxo)ethyl]-6-oxo-6,7-dihydropyrido[3',2':2,3]azepino[4,5-b]indol-5-yl}-5H-acetate (10i)

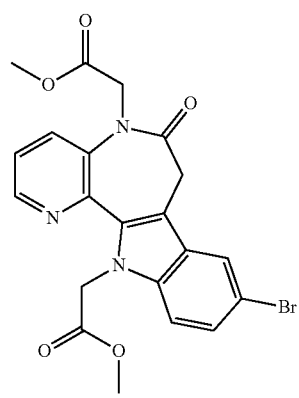

34 mg (0.1 mmol) 9-bromo-7,12-dihydropyrido[3',2':2,3]azepino[4,5-b]indol-6(5H)-one were stirred with 64 mg (0.2 mmol) cesium carbonate in dry acetone for 1 h at room temperature. 243 mg (1.6 mmol) methyl bromoacetate were added until the reaction was completed, which took overall 67 hours of stirring at room temperature. The mixture was then poured into water (5 ml), whereupon a brown material precipitated, which was filtered off to yield 26 mg (55%), m.p. 211-213° C. (dec.); IR (KBr): 3077 cm$^{-1}$ (CH-arom.), 2949 cm$^{-1}$ (CH-aliph.), 1757/1733/1670 cm$^{-1}$ (C=O); $^1$H-NMR (DMSO-d$_6$, 400 MHz): δ (ppm)=3.19 (br. s, 1H, azepine-CH$_2$), 3.64 (s, 3H, OCH$_3$), 3.66 (s, 3H, OCH$_3$), 4.12 (br. s, 1H, azepine-CH), 4.42-4.44 (m, 2H, CH$_2$), 5.22 (br. s, 1H, CH$_2$), 5.57 (br. s, 1H, CH$_2$), 7.42 (dd, 1H, 8.8/1.9 Hz, arom H.), 7.51 (dd, 1H, 8.4/4.5 Hz, arom. H), 7.62 (d, 1H, 8.8 Hz, arom. H), 7.94 (dd, 1H, 8.4/1.3 Hz, arom. H), 8.08 (d, 1H, 1.8 Hz, arom. H), 8.53 (dd, 1H, 4.5/1.3 Hz, arom. H); $^{13}$C-NMR (DMSO-d$_6$, 100.6 MHz): δ (ppm)=30.9 (azepine-CH$_2$), 46.2, 51.4 (N—CH$_2$), 51.9, 52.0 (OCH$_3$), 112.7, 121.2, 122.9, 126.5, 132.1, 145.4 (tert. arom. C), 112.5, 112.6, 132.9, 137.0, 137.5, 142.3 (quat. arom. C), 169.2, 169.6, 170.2 (C=O); C$_{21}$H$_{18}$BrN$_3$O$_5$ (472.30); purity (HPLC): 95.5% (t$_s$=4.23 min, acetonitrile/water 50:50).

7,8-Dihydro-5H-pyrido[3,2-b]azepine-6,9-dione 9-(phenylhydrazone)

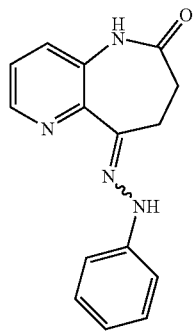

176 mg (1.0 mmol) 5H-pyrido[3,2-b]azepine-6,9(7H,8H)-dione and 162 mg (1.5 mmol) phenylhydrazine were suspended in glacial acetic acid (11 ml) and stirred for 1 hour at 70° C. After cooling to room temperature, the mixture was poured into a 5% aqueous sodium acetate solution. The mixture was extracted with 4×20 ml ethyl acetate. The combined organic layers were dried over sodium sulfate, and evaporated to dryness. Recrystallization from ethanol afforded a white solid, yield: 82 mg (32%); m.p. 206° C.; IR (KBr): 3291 cm$^{-1}$ (NH), 3060/3023 cm$^{-1}$ (CH-arom.), 2953/2885 cm$^{-1}$ (CH-aliphat.), 1676 cm$^{-1}$ (C=O); $^1$H-NMR (d$_6$-DMSO, 400 MHz): δ (ppm)=2.54-2.58 (m, 2H, part of AA'XX'-system, azepine-CH$_2$), 3.02-3.06 (m, 2H, part of AA'XX'-system, azepine-CH$_2$), 6.76-6.81 (m, 1H, arom. H), 7.17-7.23 (m, 4H, arom. H), 7.36 (dd, 1H, 8.0/4.4 Hz, arom. H), 7.39 (dd, 1H, 8.0/1.7 Hz, arom. H), 8.40 (dd, 1H, 4.7/1.7 Hz, arom. H), 9.32 (s, 1H, NH), 9.76 (s, 1H, NH); C$_{15}$H$_{14}$N$_4$O (266.31).

7,12-Dihydropyrido[3',2':2,3]azepino[4,5-b]indol-6(5H)-one (10k)

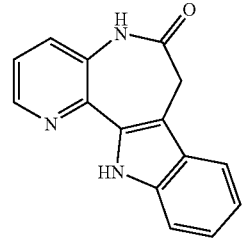

Prepared according to general procedure B from 72.4 mg (0.27 mmol) 7,8-dihydro-5H-pyrido[3,2-b]azepine-6,9-dione 9-(phenylhydrazone) in 30 ml diphenyl ether. Recrystallization from ethanol afforded a brown solid. Yield: 17 mg (25%); m.p. >330° C.; IR (KBr): 3054 cm$^{-1}$ (CH-arom.), 2974 cm$^{-1}$ (CH-aliph.), 1675 cm$^{-1}$ (C=O), $^1$H-NMR (d$_6$-DMSO, 400 MHz): δ (ppm)=3.66 (s, 2H, azepine-CH$_2$), 7.06-7.09 (m, 1H, arom. H), 7.18-7.22 (m, 1H, arom. H), 7.40 (dd, 1H, 8.2/4.5 Hz, arom. H), 7.47 (d, 1H, 8.2 Hz, arom. H), 7.62 (dd, 1H, 8.2/1.4 Hz, arom. H), 7.70 (d, 1H, 8.0 Hz, arom. H), 8.48 (dd, 1H, 4.5/1.4 Hz, arom. H), 10.22 (s, 1H, NH), 11.70 (s, 1H, NH); $^{13}$C-NMR (DMSO-d$_6$, 100.6 MHz): δ (ppm)=31.9 (azepine-CH$_2$), 111.9, 118.4, 119.1, 122.5, 122.8, 129.3, 144.3 (tert. arom. C), 108.9, 126.3, 132.0, 132.5, 137.5, 140.5 (quat. arom. C), 171.1 (C=O); C$_{15}$H$_{11}$N$_3$O (249.27); purity (HPLC): 98.8% (t$_s$=3.25 min, acetonitrile/water 35:65).

7,8-dihydro-5H-pyrido[3,2-b]azepine-6,9-dione 9-{([4-(trifluoromethyl)phenyl]hydrazone}

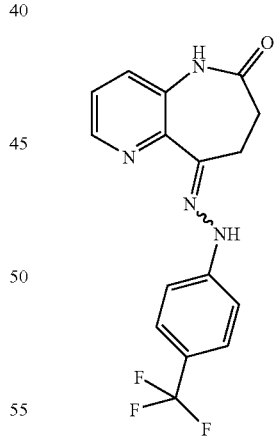

Prepared according to general procedure A from 176 mg (1.0 mmol) 5H-pyrido[3,2-b]azepine-6,9(7H,8H)-dione and 264 mg (1.5 mmol) [4-(trifluoromethyl)phenyl]hydrazine. Recrystallization from ethanol afforded a yellow solid. Yield: 196 mg (59%), m.p. 229-230° C.; IR (KBr): 3283 cm$^{-1}$ (NH), 2969/2897 cm$^{-1}$ (CH-aliph.), 1678 cm$^{-1}$ (C=O); $^1$H-NMR (d$_6$-DMSO, 400 MHz): δ (ppm)=2.58-2.61 (m, 2H, part of AA'XX'-system, azepine-CH$_2$), 3.07-3.10 (m, 2H, part of AA'XX'-system, azepine-CH$_2$), 7.35 (d, 2H, 8.6 Hz, arom. H), 7.41-7.47 (m, 2H, arom. H), 7.56 (d, 2H, 8.7 Hz, arom. H), 8.44 (dd, 1H, 4.4/1.6 Hz, arom. H), 9.84 (s, 1H, NH), 9.86 (s, 1H, NH); C$_{16}$H$_{13}$F$_3$N$_4$O (334.30)

9-Trifluoromethyl-7,12-dihydropyrido[3',2':2,3]azepino[4,5-b]indol-6(5H)-one (10l)

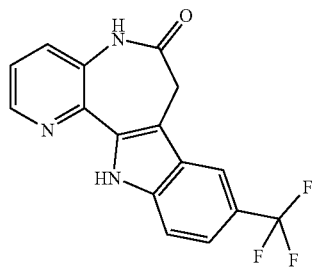

Prepared according to general procedure B from 302.5 mg (0.9 mmol) 7,8-dihydro-5H-pyrido[3,2-b]azepine-6,9-dione 9-{[4-(trifluoromethyl)phenyl]hydrazone} in 100 ml diphenyl ether. Recrystallization from ethanol afforded silver needles. Yield: 100 mg (35%); m.p. >330° C.; IR (KBr): 3200 cm$^{-1}$ (NH), 3067 cm$^{-1}$ (CH aromat.), 2978 cm$^{-1}$ (CH aliphat.), 1661 cm$^{-1}$ (C=O); $^1$H-NMR (DMSO-d$_6$, 400 MHz): δ (ppm)=3.78 (s, 2H, azepine-CH$_2$), 7.44-7.50 (m, 2H, arom. H), 7.64-7.67 (m, 2H, arom. H), 8.20 (s, 1H, arom. H), 8.52 (dd, 1H, 4.5/1.4 Hz, arom. H), 10.31 (s, 1H, NH), 12.21 (s, 1H, NH); $^{13}$C-NMR (DMSO-d$_6$, 100.6 MHz): δ (ppm)=31.6 (azepine-CH$_2$), 112.6, 116.5 (q, $^3J_{C,F}$=4.3 Hz, C—C—CF$_3$), 119.0 (q, $^3J_{C,F}$=3.3 Hz, C—C—CF$_3$), 123.1, $\overline{1}$29.5, 144.4 (tert. arom. C), 109.7, 1$\overline{2}$0.0 (q, $^2J_{C,F}$=31.3 Hz, C—CF$_3$), 125.5 (q, $^1J_{C,F}$=270.3 Hz, CF$_3$), 125.6, 132.5, 134.$\overline{6}$, 138.8, 139.7 (quat. arom. C), $\overline{1}$70.9 (C=O); C$_{16}$H$_{10}$F$_3$N$_3$O (317.237); calculated C, 60.57; H, 3.18; N, 13.24. found C, 60.33; H, 3.15; N, 13.03. purity (HPLC): 99.7% (t$_s$=8.24 min, acetonitrile/water 30:70).

7,8-Dihydro-5H-pyrido[3,2-b]azepine-6,9-dione 9-[(4-iodophenyl)hydrazone]

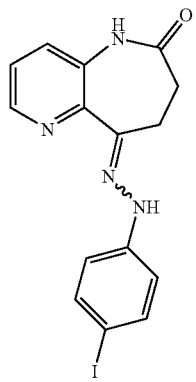

Prepared according to general procedure A from 176 mg (1.0 mmol) 5H-pyrido[3,2-b]azepine-6,9(7H,8H)-dione and 257 mg (1.5 mmol) (4-iodophenyl)hydrazine hydrochloride. Recrystallization from ethanol afforded an orange solid. Yield: 248 mg (63%); m.p. 204-205° C.; IR (KBr): 3211 cm$^{-1}$ (NH), 2964/2900 cm$^{-1}$ (CH-aliph.), 1691 cm$^{-1}$ (C=O); $^1$H-NMR (DMSO-d$_6$, 400 MHz): δ (ppm)=2.55-2.59 (m, 2H, azepine-CH$_2$, part of AA'XX'-system), 3.01-3.04 (m, 2H, azepine-CH$_2$, part of AA'XX'-system), 7.02-7.06 (m, 2H, arom. H), 7.37-7.44 (m, 2H, arom. H), 7.50-7.54 (m, 2H, arom. H), 8.41 (dd, 1H, 4.5/1.7 Hz, arom. H), 9.51 (s, 1H, NH), 9.82 (s, 1H, NH); C$_{15}$H$_{13}$IN$_4$O (392.20).

9-Iodo-7,12-dihydropyrido[3',2':2,3]azepino[4,5-b]indol-6(5H)-one (10m)

Prepared according to general procedure B from 196 mg (0.5 mmol) 7,8-dihydro-5H-pyrido[3,2-b]azepine-6,9-dione 9-[(4-iodophenyl)hydrazone] in 70 ml diphenyl ether. Recrystallization from ethanol afforded a grey solid. Yield: 49 mg (26%); m.p. >330° C.; IR (KBr): 3183 cm$^{-1}$ (NH), 3057 cm$^{-1}$ (CH-arom.), 2970/2912 cm$^{-1}$ (CH-aliph.), 1673 cm$^{-1}$ (C=O); $^1$H-NMR (DMSO-d$_6$, 400 MHz): δ (ppm)=3.66 (s, 2H, azepine-CH$_2$), 7.32 (d, 1H, 8.5 Hz, arom. H), 7.41-7.46 (m, 2H, arom. H), 7.62 (dd, 1H, 8.2/1.4 Hz, arom. H), 8.12 (d, 1H, 1.4 Hz, arom. H), 8.49 (dd, 1H, 4.5/1.4 Hz, arom. H) 10.25 (s, 1H, NH), 11.91 (s, 1H, NH); $^{13}$C-NMR (DMSO-d$_6$, 100.6 MHz): δ (ppm)=31.6 (azepine-CH$_2$), 114.3, 122.9, 127.0, 128.9, 130.7, 144.3 (tert. arom. C), 82.7, 108.0, 129.4, 132.3, 133.4, 136.4, 139.9 (quat. arom. C) 170.9 (C=O); C$_{15}$H$_{10}$IN$_3$O (375.17); purity (HPLC): 97.4% (t$_s$=9.28 min, acetonitrile/water 30:70)

EXAMPLE 2

Ins-1E Cell Proliferation Assay

The proliferation of Ins-1E insulinoma cells was determined by monitoring DNA synthesis as an indirect parameter of cell proliferation. The incorporation of the thymidine analogue 5-bromo-2'-deoxyuridine (BrdU) during replication into cellular DNA was used to label the DNA of mitotically active cells. After its incorporation into DNA, BrdU was detected by immunoassay.

10,000 Ins-1E cells were seeded per 96-well (black 96-well tissue culture plates, Falcon #353948) in 100 µl culture medium (RPMI 1640 containing 11 mM glucose, 5% FCS, 10 mM HEPES, 50 µM 2-mercaptoethanol, 1 mM MEM sodium pyruvate, 100 U/ml penicillin, 100 µg/ml streptomycin) and cultivated at 37° C., 5% CO$_2$ in humidified atmosphere for 3 days. Media was changed to 100 µl starvation medium (culture medium with only 5 mM glucose, 1% FCS) and the cells were re-incubated for 1 day. Then media was exchanged to starvation medium containing test substances and the cells were further incubated for 24 h. For the last 4 hours BrdU was added to reach a concentration of 10 µM. Cell proliferation ELISA (Cell Proliferation ELISA, BrdU, chemiluminescence, Roche, cat. No. 1669915) was performed according to the manufacturers guidelines.

EXAMPLE 3

Viability, Cell Number, Caspase Activity and DNA-Fragmentation of Apoptotic Ins-1E Cells The effects of the test compounds on beta cell function were assessed using biological assays monitoring cellular metabolic activity as well as specific apoptotic events in Ins-1E cells.

10,000 Ins-1E cells were seeded per 96-well (black 96-well tissue culture plates, Falcon #353948) in 100 µl culture medium (RPMI 1640 containing 11 mM glucose, 5% FCS, 10 mM HEPES, 50 µM 2-mercaptoethanol, 1 mM MEM sodium pyruvate, 100 U/ml penicillin, 100 µg/ml streptomycin) and cultivated at 37° C., 5% $CO_2$ in humidified atmosphere for 3 days. Media was changed to 100 µl starvation medium (culture medium with only 5 mM glucose, 1% FCS) and the cells were re-incubated for 1 day. Then media was exchanged to starvation medium containing test substances.

Apoptosis of Ins-1E cells was induced by addition of a combination of BSA coupled palmitate and glucose (pal/gluc) or a combination of cytokines (cyt) 1 hour after starting the treatment with test substances: pal/gluc: 0.3 mM palmitate:BSA (palmitic acid sodium salt:fatty acid free BSA 6:1) and 25 mM glucose. 10×cyt: 0.04 ng/ml IL-1β and 1 ng/ml IFNγ. The cells were further incubated with test substances and apoptotic inducer for 24 hours.

Viability was assessed by mitochondric reduction of the non toxic dye Alamar Blue (Bioscource, cat. No. DAL1025). The dye was added to the cells 4 hours before read-out according to the manufacturers guidelines. Basal fluorescence was measured immediately to be subtracted from the fluorescence after 4 hours. The plates were washed 1 time with 200 µl PBS and frozen at −80° C. for at least 1 hour to be used for the cell number determination assay.

Cell number was measured by staining of cellular DNA with CyQuant dye (CyQuant Cell Proliferation Assay Kit, Molecular Probes, cat. No. C-7026) which becomes fluorescent when bound to DNA. The assay was performed according to the manufacturers guidelines.

Caspase activity is a characteristic of early apoptotic cells. Their activity was quantified by an enzymatic assay (homogeneous caspases assay, Roche, cat. No. 03 005 372 001). Caspase activity was measured 3 hours after addition of caspases substrate according to the manufacturers guidelines.

DNA-fragmentation is a late apoptotic event comprising storage of nucleosomal DNA-fragments as mono- and oligo nucleosomes in the cytoplasm. Their concentration was determined by ELISA (Cell death detection ELISA, Roche, cat. No. 1774425) according to the manufacturers guidelines.

FIGS. 1-9 and 12-13 show that the test compounds 4-azakenpaullone (FIG. 1, 2), 10c (FIG. 3, 4), 10a (FIG. 5, 6), 10d (FIG. 7), 10e (FIG. 8, 9) and 10l (FIG. 12, 13) are capable of stimulating proliferation and/or inhibiting apoptotic processes in Ins-1E cells.

EXAMPLE 4

Increase of Pax4 Transcription in Rat Insulinoma Cells

The response of the Pax4 gene to test compounds was investigated in the rat insulinoma cell line INS-1E. INS-1E cells are known to express Pax4 and to upregulate Pax4 levels in response to the treatment with activin-A and betacellulin. In the search for novel beta cell mitogens and/or beta cell protective agents the inventors treated INS-1E cells with test compound 10c. Compound 10c induces the relative Pax4 expression about 5-fold compared to the control and compared to 1 nM activin A (FIG. 11).

Cell Culture

INS-1E cells were cultured as described (Merglen, (2004) Endocrinology; 145: 667-678). Cells were seeded at a density of $2 \times 10^4$ cells per $cm^2$ 6 to 8 days before the treatment with chemicals. During the growth period the medium was changed once. The cells were incubated for different periods of time with chemicals under serum-free conditions. The cells were harvested in Qiagen RNAeasy cell lysate buffer and immediately transferred to dry ice. The samples were stored at −20° C. until RNA isolation was carried out.

Quantitative RT-PCR

Total RNA from $8 \times 10^4$ cells growing on 4 $cm^2$ surface area of a tissue culture dish was extracted using Qiagen RNAeasy kit according to the instructions of the manufacturer (Qiagen) and 2 µg was converted into cDNA. Primers for pax4, 18S RNA, and rat RNA polymerase II largest subunit (RPB1) were designed using the Primer Express 1.5 Software from Applied Biosystems and sequences can be obtained upon request. Quantitative real-time PCR was performed using Applied Biosystems SDS 7000 detection system. Amplifications from 2 independent experiments were performed in duplicate for each transcript and mean values were normalized to the mean value of the reference RNA 18S RNA.

EXAMPLE 5

Replication of Primary Rat Beta Cells

Compound 10c stimulates the replication of primary rat beta cells in culture (FIG. 16). Isolated rat islets were cultured for 72 hours in the presence of compound 10c before the islets were disaggregated and dispersed on microscope slides. Replicating beta cells were identified by immunohistological staining of dispersed islets with antibodies against C-peptide, a proteolytic fragment of proinsulin, and the cell division marker Ki-67.

In Vitro Beta Cell Proliferation Assay

Islets of Langerhans are isolated by standard Liberase digestion method from rat pancreata (Liberase™ Cl enzyme blend BMB Cat. #1814-435, ROCHE).

Freshly isolated islets are cultured in vitro with or without the addition of the factor of interest for 48 h. Following the culture period the islets are dispersed gently by titration in $Ca^{2+}$ and $Mg^{2+}$ free PBS. The resulting single cell suspension is applied to adhesive slides at 3000-6000 cells per well (Adhesion slides/Fa Superior Marienfeld REF 09 000 00/). The adherent islet cells are fixed and stained by standard immunofluorescence techniques for C-peptide, a fragment of proinsulin and Ki-67 a marker of proliferating cells.

An Olympus microscope equipped with an automatic image acquisition device (Olympus) is used for counting of C-peptide positive beta cells. Proliferating C-peptide/Ki-67 double positive beta cells are counted manually. Thereby the fraction of proliferating beta cells can be determined.

EXAMPLE 6

Compounds 10c and e are structurally very similar to 1-Azakenpaullone and differ only by one substituent at position 9 of the D ring from their template 1-Azakenpaullone. In order to investigate if 10c and e selectively inhibit the enzymatic activity of the GSK3 isoforms or theses of other kinases as well both compounds and 1-Azakenpaullone (DG 340002) were tested in parallel against a panel of 28 protein kinases in biochemical kinase activity assays (FIG. 14). These kinases were selected among about 250 different kinases based on their structural or functional similarity to GSK3, e.g. all available members of the CDK family were included in the survey because CDKs are most similar to GSK3 and several kinase inhibitors are known that inhibit members of both families. The direct comparison of different compounds in such an experiment provides information on the relative selectivity of the respective compounds. The data indicate that the compounds 10c and e show a similar activity profile as 1-Azakenpaullone, though compound 10e also significantly inhibits cyclin-dependent kinases (CDKs).

FIG. 15 indicates that compound 10c is a potent inhibitor of human glycogen synthase 3, whereas comparatively higher concentration of this inhibitor are required to inhibit the enzymatic activity of cyclin dependent kinase 1. Compound 10c, however, still has a higher affinity to CDK1 than the reference compound 1-Azakenpaullone.

The invention claimed is:

1. A compound of formula (Ib) or (Ic)

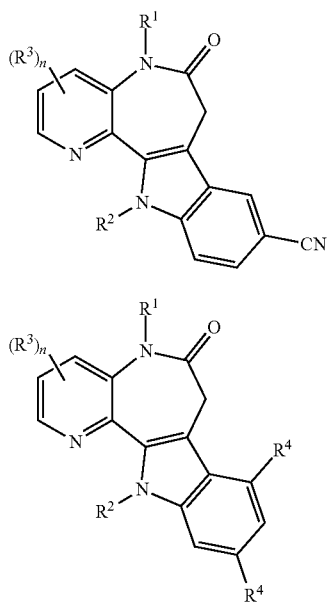

wherein R1 and R2 are independently H, —$C_1$-$C_6$ alkyl, optionally substituted, or —CO—$C_1$-$C_6$ alkyl, optionally substituted, wherein the substituents are independently one or more of halo, CN, OH, O—$C_1$-$C_6$ alkyl; COOH, COO—$C_1$-$C_6$ alkyl, —$CONH_2$, —CONH($C_1$-$C_6$)alkyl, —CON($C_1$-$C_6$ alkyl)$_2$, aryl, heteroaryl that is benzofuranyl, furyl, thienyl, benzothienyl, thiazol, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolynyl, purinyl, carbazolyl, benzoxazolyl, benzamidazolyl, indolyl, isoindolyl, pyrazinyl, diazinyl, tetrazinyl or tetrazolyl, or polyoxyethylenyl or combinations thereof;

each R3 and R4 is independently $C_1$-$C_6$ alkyl, —$C_2$-$C_6$ alkenyl; —$C_2$-$C_6$ alkynyl; —$C_3$-$C_{10}$ cycloalkyl, —$C_3$-$C_{10}$ heterocyclyl, that is mono- or polycyclic saturated or unsaturated heterocyclyl groups with 1 to 4 hetero atoms selected from N, S and O, with the remainder of the ring atoms being carbon atoms and having a total number of ring atoms of 3 to 10, aryl with 6 to 10 carbon atoms, heteroaryl that is benzofuranyl, furyl, thienyl, benzothienyl, thiazol, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolynyl, purinyl, carbazolyl, benzoxazolyl, benzamidazolyl, indolyl, isoindolyl, pyrazinyl, diazinyl, tetrazinyl or tetrazolyl, each optionally substituted; halo, —$NO_2$, —CN, —OR1; —COOR1 or —NR1R2; wherein R1 and R2 are as defined above; and wherein alkyl, alkenyl or alkynyl is optionally substituted with one or more of halo, —$NO_2$, —CN, —OR1, COOR1, —OCOR1, —NR1R2, NR1COR2, —NR1OCOR2, —NR1CONR1R2, —SR1, SOR1, —$SO_2$R1, —SONR1R2, —$SO_2$NR1R2 or —NR1$SO_2$NR1NR2; or combinations thereof, wherein R1 and R2 are as defined above;

wherein cycloalkyl, heterocyclyl, aryl or heteroaryl is optionally substituted with one or more of $C_1$-$C_6$ alkyl, halo, —$NO_2$, —CN, —OR1, COOR1, —OCOR1, —NR1R2, NR1COR2, —NR1OCOR2, —NR1CONR1R2, —SR1, SOR1, —$SO_2$R1, —SONR1R2, $SO_2$NR1R2 or —NR1$SO_2$NR1NR2; or combinations thereof, wherein R1 and R2 are as defined above;

n=0-3.

2. The compound of claim 1, wherein R1 is H or $C_1$-$C_2$ alkyl optionally substituted.

3. The compound of claim 1, wherein R2 is H or $C_1$-$C_2$ alkyl optionally substituted.

4. The compound of claim 1, wherein R4 is selected from R' or OR1', wherein R1' is H or $C_1$-$C_4$-alkyl optionally halogenated; COOR1", wherein R1" is selected from H, $C_1$-$C_4$-alkyl or aryl; CN or halo.

5. The compound of claim 1, wherein R4 is CN.

6. A pharmaceutical composition comprising as an active agent a compound of claim 1, and pharmaceutically acceptable carriers, diluents or adjuvants.

* * * * *